United States Patent
Albaugh et al.

(10) Patent No.: US 7,109,351 B1
(45) Date of Patent: Sep. 19, 2006

(54) FUSED PYRROLECARBOXAMIDES; GABA BRAIN RECEPTOR LIGANDS

(75) Inventors: Pamela Albaugh, Clinton, CT (US); Kenneth Shaw, Weston, CT (US); Alan Hutchison, Madison, CT (US)

(73) Assignee: Neurogen Corporation, Branford, CT (US)

(*) Notice: Subject to any disclaimer, the term of this patent is extended or adjusted under 35 U.S.C. 154(b) by 0 days.

(21) Appl. No.: 09/651,207

(22) Filed: Aug. 30, 2000

Related U.S. Application Data

(63) Continuation-in-part of application No. 09/387,311, filed on Aug. 31, 1999, now abandoned.

(51) Int. Cl.
*C07D 209/42* (2006.01)
*A61K 31/40* (2006.01)

(52) U.S. Cl. ...................................... 548/492; 514/419
(58) Field of Classification Search ................ 548/492, 548/465; 514/414, 419
See application file for complete search history.

(56) References Cited

U.S. PATENT DOCUMENTS

| | | | |
|---|---|---|---|
| 3,455,943 A | 7/1969 | Remers et al. ........... 548/505 X |
| 4,075,343 A | 2/1978 | Kadin ......................... 424/258 |
| 4,435,403 A | 3/1984 | Baestrup et al. ............. 424/256 |
| 4,442,295 A | 4/1984 | Michel et al. ............... 548/505 |
| 4,564,610 A | 1/1986 | Rahtz et al. .................. 514/80 |
| 4,596,808 A | 6/1986 | Braestrup et al. ............ 514/292 |
| 4,623,649 A | 11/1986 | Huth et al. ................... 514/292 |
| 4,719,210 A | 1/1988 | Seidelmann et al. ........ 514/222 |
| 4,736,043 A | 4/1988 | Michel et al. ............... 548/492 |
| 5,216,159 A | 6/1993 | Thurkauf et al. ............ 544/250 |
| 5,243,049 A | 9/1993 | Shaw et al. .................... 546/84 |
| 5,266,698 A | 11/1993 | Shaw et al. ................... 544/346 |
| 5,484,944 A * | 1/1996 | Albaugh et al. .............. 546/171 |
| 5,608,079 A | 3/1997 | Albaugh et al. .............. 548/492 |
| 5,677,309 A | 10/1997 | Chen et al. |
| 5,723,462 A | 3/1998 | Albaugh et al. |
| 5,750,702 A * | 5/1998 | Albaugh et al. .............. 546/183 |
| 5,804,686 A * | 9/1998 | Albaugh et al. .............. 548/516 |
| 5,925,770 A | 7/1999 | Albaugh et al. |
| 5,955,465 A | 9/1999 | Chen et al. |
| 6,080,873 A | 6/2000 | Albaugh et al. .............. 548/516 |
| 6,211,365 B1 * | 4/2001 | Albaugh et al. .............. 544/144 |
| 6,353,109 B1 * | 3/2002 | Albaugh et al. ........... 546/277.4 |
| 6,515,140 B1 | 2/2003 | Albaugh et al. |

FOREIGN PATENT DOCUMENTS

| | | |
|---|---|---|
| DE | 3246932 | 6/1984 |
| EP | 0 054 507 | 6/1982 |
| EP | 183 458 | 6/1986 |
| WO | WO 93/17025 | 9/1993 |
| WO | WO 94/17095 | 8/1994 |
| WO | WO 95/11885 | 5/1995 |
| WO | WO 97/26243 | 7/1997 |
| WO | WO 97/34870 | 9/1997 |
| WO | WO 98/02420 | 1/1998 |
| WO | WO 99/25684 | 5/1999 |
| WO | 9925684 * | 5/1999 |
| WO | 9734670 * | 9/1999 |

OTHER PUBLICATIONS

Biere et al., *Liebigs Ann. Chem.*, pp. 1749–1764. (1986), "Teach assorted benzodiazepine agonists and antagonists and related anti-depressant and central nervous system active compounds."

Carlock et al., *J. Org. Chem.*, vol. 42, No. 11, pp. 1883–1885. (1977), "3-Diazo-4-oxo-3,4-dihydroquinoline. A Novel Synthon for Indole 3-carboxamides."

Carlock et al., *J. Heterocyclic Chem.*, vol. 14, pp. 519–520. (1977), "A Noteworthy Improvement of the 3-Diazo-4-oxo-3,4-dihydroquinoline Photosynthesis of Indole-3-carboxamides."

* cited by examiner

*Primary Examiner*—Deborah C. Lambkin
(74) *Attorney, Agent, or Firm*—McDonnell Boehnen; Hulbert & Berghoff LLP

(57) ABSTRACT

Substituted pyrrolecarboxamide compounds are disclosed. These compounds are highly selective agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Alzheimer's dementia, sleep and seizure disorders, overdose with benzodiazepine drugs and for enhancement of memory. Pharmaceutical compositions, including packaged pharmaceutical compositions, are further provided. Compounds of the invention are also useful as probes for the localization of $GABA_A$ receptors in tissue samples.

36 Claims, No Drawings

FUSED PYRROLECARBOXAMIDES; GABA BRAIN RECEPTOR LIGANDS

This application is a continuation-in-part of U.S. Ser. No. 09/387,311, filed Aug. 31, 1999, now abandoned.

BACKGROUND OF THE INVENTION

1. Field of the Invention

This invention relates to fused pyrrolecarboxamides. This invention also relates to pharmaceutical compositions comprising such compounds and to the use of such compounds in treatment of certain central nervous system (CNS) diseases. This invention also relates to the use of these fused pyrrolecarboxamide compounds in combination with one or more other CNS agents to potentiate the effects of the other CNS agents. Additionally this invention relates to the use such compounds as probes for the localization of $GABA_A$ receptors in tissue sections.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6th ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

Various compounds have been prepared as benzodiazepine agonists and antagonists. For Example, U.S. Pat. Nos. 3,455,943, 4,435,403, 4,596,808, 4,623,649, and 4,719,210, German Patent No. DE 3,246,932, and Liebigs Ann. Chem. 1986, 1749 teach assorted benzodiazepine agonists and antagonists and related anti-depressant and central nervous system active compounds.

U.S. Pat. No. 3,455,943 disclosed indole derivatives.

Other references, such as U.S. Pat. No. 4,435,403 and German patent DE 3,246,932 disclose pyrimidino[5,4-b] indoles and beta-carboline derivatives.

A variety of indole-3-carboxamides is described in the literature. See, for example, J. Org. Chem., 42: 1883–1885 (1977); J. Heterocylic Chem., 14: 519–520 (1977). Also, U.S. Pat. Nos. 5,804,686 and 6,080,873 and PCT International Publication WO 97/26243, all of which are assigned to Neurogen Corporation, disclose fused pyrrolecarboxamides.

SUMMARY OF THE INVENTION

In a preferred aspect, this invention provides pyrrolecarboxamides that bind with high affinity and high selectivity to the benzodiazepine site of the $GABA_A$ receptor, including human $GABA_A$ receptors.

Thus, the invention provides compounds of Formula I (shown below), and pharmaceutical compositions comprising compounds of Formula I.

The invention further comprises methods of treating patients suffering from CNS disorders with an effective amount of a compound of the invention. The patient may be a human or other mammal. Treatment of humans, domesticated companion animals (pet) or livestock animals suffering from CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of the formula

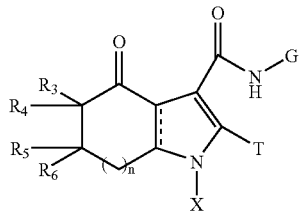
I or the pharmaceutically acceptable salts thereof wherein:
T is halogen, hydrogen, hydroxyl, amino, alkyl or alkoxy;
X is hydrogen, hydroxy, amino, benzyl, t-butoxycarbonyl, benzyloxycarbonyl, alkyl, or alkoxy;
G represents

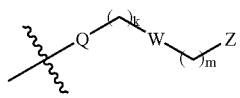

where

Q is an optionally substituted aryl or optionally substituted heteroaryl group having from 1 to 3 rings, 3 to 8 members in each ring and from 1 to 3 heteroatoms;

W is chosen from hydrogen, —O—, —NH—, —NR$_7$—, —S(O)$_{0-2}$—, —C(=O)—, —OC(=O)—, —C(=O)O—, —C(=O)NH—, —NHC(=O)—, —NR$_7$C(=O)—, —NHS(O)$_{0-2}$—, —NR$_7$S(O)$_{0-2}$—, —S(O)$_{0-2}$NH—, —S(O)$_{0-2}$NR$_7$—, and CR$_7$R$_8$ where R$_7$ and R$_8$ are the same or different and represent hydrogen, alkyl, or CR$_7$R$_8$ represents a cyclic moiety having 3–7 carbon atoms, wherein W may not be hydrogen when Q is phenyl, 2- or 3-thienyl, or 2-, 3-, or 4 pyridyl, indolyl, imidazolyl, or pyridazinyl;

Z is hydrogen, hydroxy, cycloalkyl(alkoxy), amino, mono- or di(alkyl$_1$)amino, azacycloalkyl, —O(alkyl$_1$), —S(O)$_{0-2}$(alkyl$_1$), —C(=O)(alkyl$_1$), —OC(=O)(alkyl$_1$), —OC(=O)H, —C(=O)O(alkyl$_1$), —C(=O)OH, —C(=O)NH(alkyl$_1$), —C(=O)N(alkyl$_1$)$_2$, —C(=O)NH$_2$, —NHC(=O)(alkyl$_1$), —NHC(=O)H, —N(alkyl$_1$)C(=O)(alkyl$_1$), —NHS(O)$_{0-2}$(alkyl$_1$), —N(alkyl$_1$)S(O)$_{0-2}$(alkyl$_1$), —S(O)$_{0-2}$NH(alkyl$_1$), —S(O)$_{0-2}$(alkyl$_1$)N(alkyl$_1$),
  wherein each alkyl$_1$ is independently straight, branched, or cyclic, may contain one or two double and/or triple bonds or combinations thereof, and is unsubstituted or substituted with one or more substituents independently selected from hydroxy, oxo, halogen, amino, cyano, nitro, and alkoxy, or Z is —N(R$_N$)$_2$S(O)$_{0-2}$(R$_S$) where
  each R$_N$ is independently hydrogen or alkyl where the alkyl is straight, branched, or cyclic, may contain one or two double and/or triple bonds, and is unsubstituted or substituted with one or more substituents independently selected from hydroxy, oxo, halogen, amino, cyano, nitro, and alkoxy,
  R$_S$ is hydroxy, alkoxy, heteroaryl, aryl, or alkyl where each aryl and heteroaryl is optionally substituted with one or two of alkyl, hydroxy, alkoxy, trifluoromethyl, halogen, amino, or mono- or dialkylamino; and
  each alkyl is optionally substituted with hydroxy, alkoxy, trifluoromethyl, halogen, amino, mono- or di-alkylamino, aryl, or heteroaryl; or Z is phenyl or phenylalkyl where the phenyl portion is optionally substituted with alkyl, hydroxy, alkoxy, trifluoromethyl, halogen, amino, or mono- or dialkylamino, or Z is 2-, 3-, or 4-pyridyl, 1- or 2-imidazolyl, 1-, 2-, or 3-pyrrolyl, azeditinyl, norborn-2-yl, or adamantan-2-yl; each of which may be substituted on a tertiary carbon or a secondary nitrogen with C$_1$–C$_6$alkyl, or Z is NR$_9$COR$_{10}$ where R$_9$ and R$_{10}$ are the same or different and represent hydrogen or alkyl or cycloalkyl, or Z is connected, optionally through W, to Q to form a 1–6 membered ring; or Z represents a group of the formula:

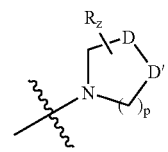

where
p is 1, 2, or 3;
D and D' independently represent oxygen, NR$_y$ or CHR$_y$, provided that only one of D and D' may be NR$_y$, and only one of D and D' may be oxygen, where each R$_y$ is hydrogen or alkyl; and
R$_z$ is hydrogen or alkyl, or Z represents a group of the formula:

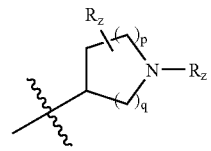

where
p is 1, 2, or 3;
q is 0, 1, or 2;
each R$_z$ is independently hydrogen or alkyl; or Z represents a group of the formula:

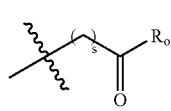

where
s is 0, 1, 2 or 3, and the sum of s and m is not less than 1;
R$_o$ is hydroxy, C$_1$–C$_6$alkoxy, amino, mono- or dialkylamino where each alkyl is independently optionally substituted with amino, or mono- or dialkylamino, or
R$_o$ is a group of the formula

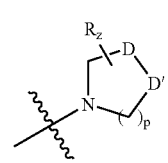

where p, D, D', and $R_z$ are as defined above;

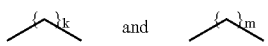

independently represent a carbon chain optionally substituted with halogen, oxo, cyano, nitro, amino, mono or dialkylamino, alkyl, alkenyl, alkynyl, trifluoromethyl, trifluoromethoxy, or cycloalkyl; wherein
  k is 0, 1, 2, or 3;
  m is 0, 1, 2, or 3; and

represents a carbon chain optionally substituted with $R_5$ and $R_6$ and n is 0, 1, 2, or 3; and $R_3$, $R_4$, $R_5$, and $R_6$ are the same or different and are independently selected at each occurrence from hydrogen, alkyl, —$COR_{11}$ or —$CO_2R_{11}$ where $R_{11}$ is alkyl or cycloalkyl having 3–7 carbon atoms; or —$CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or $R_3$ and $R_4$ together with the carbon atom to which they are attached form a cyclic moiety having 3–7 carbon atoms; or $R_5$ and $R_6$ together with the carbon atom to which they are attached form a cyclic moiety having 3–7 carbon atoms;
  where each alkyl group forming an $R_3$, $R_4$, $R_5$, or $R_6$ substituent or portion thereof may be substituted independently with hydroxy or mono- or dialkylamino where each alkyl is independently alkyl or cycloalkyl.

In another aspect, the invention provides intermediates useful for preparing compounds of Formula I.

DETAILED DESCRIPTION OF THE INVENTION

In addition to compounds of Formula I described above, the invention also encompasses compounds of the same general formula and the pharmaceutically acceptable salts thereof, wherein:

T is halogen, hydrogen, hydroxyl, $C_1$–$C_6$ amino, alkyl or $C_1$–$C_6$ alkoxy;

X is hydrogen, hydroxy, amino, $C_1$–$C_6$ alkyl, or $C_1$–$C_6$ alkoxy;

G represents

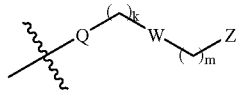

where
Q is phenyl, 2- or 3-thienyl, or 2-, 3-, or 4 pyridyl, 2-, 4-, or 5-pyrimidinyl, indolyl, imidazolyl, pyridazinyl, 1,4-benzodioxazinyl, 1,3-benzodioxolyl or imidazo[1,2-a]pyridinyl, all of which may be substituted by one or more of hydroxy, halogen, $C_1$–$C_6$ alkyl, $C_1$–$C_6$ alkoxy, cyano, nitro, amino, and mono- or dialkyl($C_1$–$C_6$) amino;

W is chosen from hydrogen, —O—, —NH—, —$NR_7$—, —$S(O)_{0-2}$—, —C(=O)—, —OC(=O)—, —C(=O) O—, —C(=O)NH—, —NHC(=O)—, —$NR_7$C (=O)—, —$NHS(O)_{0-2}$—, —$NR_7S(O)_{0-2}$—, —$S(O)_{0-2}$NH—, —$S(O)_{0-2}R_7H$—, and $CR_7R_8$ where $R_7$ and $R_8$ are the same or different and represent hydrogen, alkyl, or $R_7$–$R_8$ taken together represents a cyclic moiety having 3–7 carbon atoms, wherein W may not be hydrogen when Q is phenyl, 2- or 3-thienyl, or 2-, 3-, or 4 pyridyl, indolyl, imidazolyl, or pyridazinyl;

Z is hydrogen, hydroxy, $C_3$–$C_7$ cycloalkyl($C_1$–$C_6$ alkoxy), amino, mono- or di($C_1$–$C_6$ alkyl$_1$)amino, or $C_3$–$C_7$ azacycloalkyl, —O($C_1$–$C_6$ alkyl$_1$), —$S(O)_{0-2}$ ($C_1$–$C_6$ alkyl$_1$), —C(=O) ($C_1$–$C_6$ alkyl$_1$), —OC(=O) ($C_1$–$C_6$ alkyl$_1$), —OC(=O)H, —C(=O)O($C_1$–$C_6$ alkyl$_1$), —C(=O)OH, —C(=O)NH($C_1$–$C_6$ alkyl$_1$), —C(=O)NH$_2$, —NHC(=O) ($C_1$–$C_6$ alkyl$_1$), —NHC (=O)H, —N($C_1$–$C_6$ alkyl$_1$)C(=O) ($C_1$–$C_6$ alkyl$_1$), —$NHS(O)_{0-2}$($C_1$–$C_6$ alkyl$_1$), —N($C_1$–$C_6$ alkyl$_1$) $S(O)_{0-2}$ ($C_1$–$C_6$ alkyl$_1$), —$S(O)_{0-2}$NH($C_1$–$C_6$ alkyl$_1$), or —$S(O)_{0-2}$($C_1$–$C_6$ alkyl$_1$)N($C_1$–$C_6$alkyl$_1$),
  wherein $C_1$–$C_6$ alkyl$_1$ is independently chosen at each occurrence and is straight, branched, or cyclic, may contain one or two double and/or triple bonds, and is unsubstituted or substituted with one or more substituents selected from hydroxy, oxo, halogen, amino, cyano, nitro, and alkoxy, or Z is —$N(R_N)_2S(O)_{0-2}(R_S)$ where
  each $R_N$ is independently hydrogen or alkyl where the alkyl is straight, branched, or cyclic, may contain one or two double and/or triple bonds, and is unsubstituted or substituted with one or more substituents independently selected from hydroxy, oxo, halogen, amino, cyano, nitro, and alkoxy,
  $R_S$ is hydroxy, alkoxy, or alkyl where the alkyl is optionally substituted with hydroxy, alkoxy, trifluoromethyl, halogen, amino, mono- or dialkylamino, aryl or heteroaryl, Z is phenyl or phenyl($C_1$–$C_6$)alkyl where the phenyl portion is optionally substituted with $C_1$–$C_6$ alkyl, hydroxy, $C_1$–$C_6$ alkoxy, trifluoromethyl, trifluoromethoxy, halogen, amino, or mono- or di$C_1$–$C_6$ alkylamino, or Z is 2-, 3-, or 4-pyridyl, 1- or 2-imidazolyl, 1-, 2-, or 3-pyrrolyl, or adamantane-2-yl; each of which may be substituted on a tertiary carbon or a secondary nitrogen with $C_1$–$C_6$alkyl, or Z is $NR_9COR_{10}$ where $R_9$ and $R_{10}$ are the same or different and represent hydrogen or $C_1$–$C_6$ alkyl or $C_3$–$C_7$ cycloalkyl, or Z is connected, optionally through W, to Q to from a 1–6 membered ring; or Z represents a group of the formula:

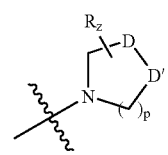

where
p is 1, 2, or 3;
D and D' independently represent oxygen, $NR_y$ or $CHR_y$, provided that only one of D and D' may be $NR_y$ where each $R_y$ is hydrogen or $C_1$–$C_6$ alkyl; or and $R_z$ is hydrogen or $C_1$–$C_6$ alkyl, or Z represents a group of the formula:

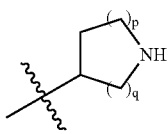

where
p is 1, 2, or 3;
q is 0, 1, or 2;
$R_z$ is hydrogen or $C_1$–$C_6$ alkyl; or
a group of the formula:

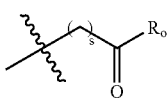

where
s is 0, 1, 2 or 3, and the sum of s and m is not less than 1;
$R_o$ is hydroxy, $C_1$–$C_6$alkoxy, amino, mono- or $diC_1$–$C_6$alkylamino where each alkyl is independently optionally substituted with amino, mono- or $diC_1$–$C_6$alkylamino, or
$R_o$ is a group of the formula

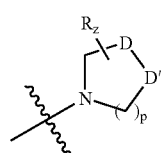

where p, D, D', and $R_z$ are as defined above;

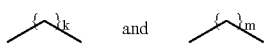

independently represent a carbon chain optionally substituted with hydrogen, halogen, oxo, cyano, nitro, amino, mono or $di(C_1$–$C_6)$alkylamino, straight or branched chain $C_1$–$C_6$ alkyl, $C_2$–$C_6$ alkenyl, $C_2$–$C_6$ alkynyl, trifluoromethyl, trifluoromethoxy, or $cycloC_1$–$C_6$ alkyl;
wherein
k is 0, 1, 2, or 3;
m is 0, 1, 2, or 3; and

represents a carbon chain optionally substituted with $R_5$ and $R_6$ and n is 0, 1, 2, or 3;
$R_3$, $R_4$, $R_5$, and $R_6$ are the same or different and are independently selected at each occurrence from hydrogen, $C_1$–$C_6$ alkyl, —$COR_{11}$ or —$CO_2R_{11}$ where $R_{11}$ is $C_1$–$C_6$alkyl or $C_3$–$C_7$ cycloalkyl; or
—$CONR_{12}R_{13}$ where $R_{12}$ and $R_{13}$ are selected independently from hydrogen, $C_1$–$C_6$ alkyl, $C_3$–$C_7$ cycloalkyl, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or
$R_3$ and $R_4$ together with the carbon atom to which they are attached form a cyclic moiety having 3–7 carbon atoms; or $R_5$ and $R_6$ together with the carbon atom to which they are attached form a cyclic moiety having 3–7 carbon atoms; and where each alkyl group forming an $R_3$, $R_4$, $R_5$, or $R_6$ substituent or portion thereof may be substituted independently with hydroxy or mono- or dialkylamino where each alkyl is independently $C_3$–$C_7$ alkyl or cycloalkyl having 3–7 carbon atoms.

Such compounds will be referred to as compounds of Formula Ia. Particular compounds of the invention also include compounds of Formula I where Q is phenyl or pyridyl (compounds of Formula Ib) and compounds of Formula I where Q is phenyl or pyridyl; and either the group

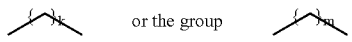

is substituted by oxo (compounds of Formula Ic).

When W is hydrogen, m is 0 and Z is absent resulting in Q groups that are optionally substituted with alkyl where the alkyl is optionally substituted as defined above.

In addition, the present invention encompasses compounds of Formula II:

Formula II

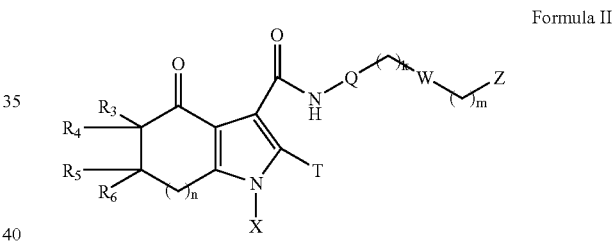

and the pharmaceutically acceptable salts thereof:

wherein n, k, m, $R_3$–$R_6$, X, T, W, and Z are defined as for Formula I;
Q is phenyl or pyridyl substituted by up to 4 groups Y, where Y is independently selected at each occurrence from hydrogen, hydroxy, halogen, $C_1$–$C_6$ alkyl, $C_1$–$C_6$ alkoxy, cyano, nitro, amino, and mono- or dialkyl($C_1$–$C_6$)amino. Compounds of Formula II, include compounds of Formula IIa, Formula IIb, Formula IIc, and Formula IId shown below Formula IIa Formula IIb

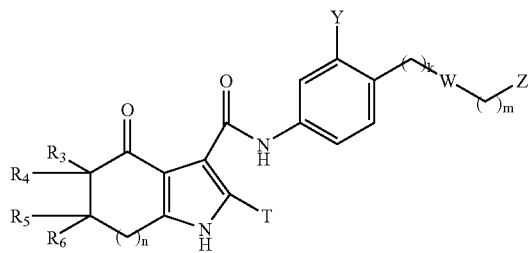

Formula IIc

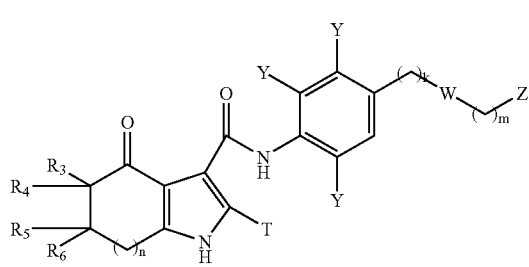

Formula IId

The present invention also encompasses compounds of Formula III

Formula III

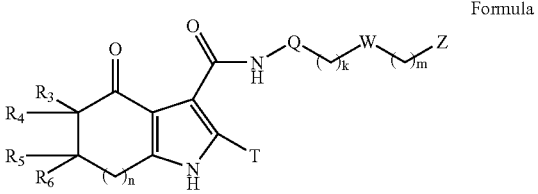

and the pharmaceutically acceptable salts thereof:

wherein n, k, m, $R_3$–$R_6$, X, T, W, and Z are defined as for Formula I;

Q is phenyl or pyridyl substituted by up to 4 groups Y, where Y is independently selected at each occurrence from hydrogen, hydroxy, halogen, $C_1$–$C_6$ alkyl, $C_1$–$C_6$ alkoxy, cyano, nitro, amino, and mono- or dialkyl($C_1$–$C_6$)amino. Particular compounds of Formula III include compounds of Formula IIIa and Formula IIIb shown below.

Formula IIIa

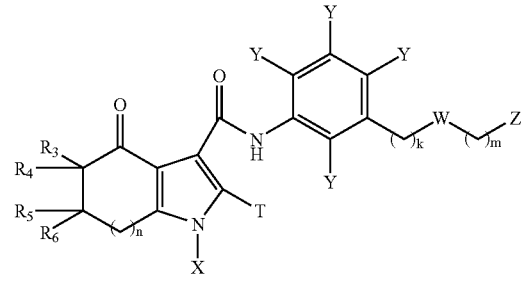

Formula IIIb

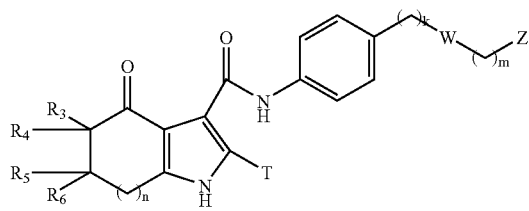

The present invention also encompasses compounds of Formula IV

Formula IV

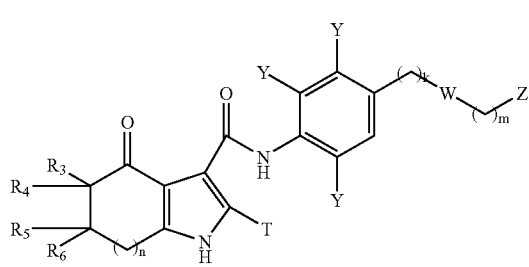

and the pharmaceutically acceptable salts thereof:

wherein n, m, $R_3$–$R_6$, X, T, W, and Z are defined as for Formula I;

Q is phenyl or pyridyl substituted by up to 4 groups Y, where Y is independently selected at each occurrence from hydrogen, hydroxy, halogen, $C_1$–$C_6$ alkyl, $C_1$–$C_6$ alkoxy, cyano, nitro, amino, and mono- or dialkyl($C_1$–$C_6$)amino. Particularly included as compounds of Formula IV are compounds of Formula IV-1, Formula IV-2, and Formula IV-3, shown below.

Formula IV-1

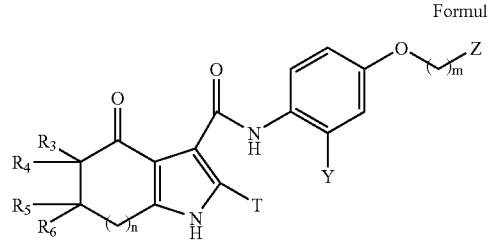

-continued

Formula IV-2

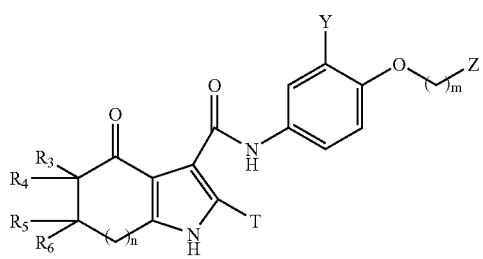

Formula IV-3

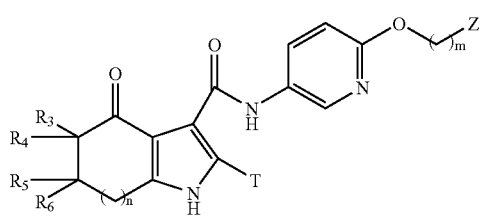

Preferred compounds of Formula IV, IV-1, IV-2, and IV-3 are those compounds where Z is a group —OR and R is hydrogen or alkyl wherein the alkyl is straight, branched, or cyclic, may contain one or two double and/or triple bonds, and is unsubstituted or substituted with one or more substituents selected from: hydroxy, oxo, halogen, amino, cyano, nitro, and alkoxy.

Other preferred compounds of Formula IV, IV-1, IV-2, and IV-3 are those compounds where Z is a group —NR$_a$R$_b$ wherein R$_a$ and R$_b$ are independently hydrogen or alkyl wherein each alkyl is independently straight, branched, or cyclic, may contain one or two double and/or triple bonds, and is unsubstituted or substituted with one or more substituents selected from: hydroxy, oxo, halogen, amino, cyano, nitro, and alkoxy; or R$_a$ and R$_b$ may be joined to form a heterocycloalkyl ring.

Further included as compounds of Formula IV are compounds of Formula IVa and IVb:

Formula IVa

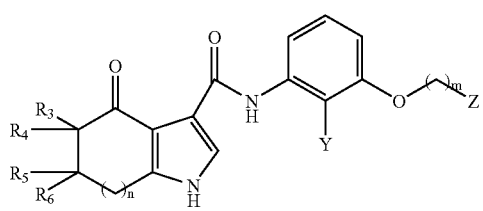

Formula IVb

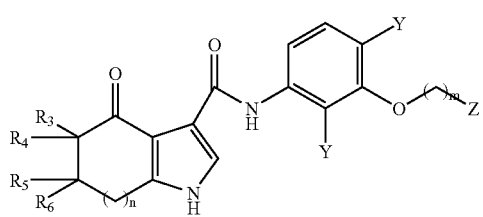

The present invention also encompasses compounds of Formula V.

Formula V

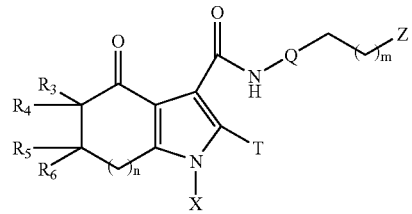

wherein n, m, R$_3$–R$_6$, X, T, W, and Z are defined as for Formula I;

Q is phenyl or pyridyl substituted by up to 4 groups Y, where Y is independently selected at each occurrence from hydrogen, hydroxy, halogen, C$_1$–C$_6$ alkyl, C$_1$–C$_6$ alkoxy, cyano, nitro, amino, and mono- or dialkyl(C$_1$–C$_6$)amino.

Particularly included as compounds of Formula V are compounds of Formula Va, Formula Vb Formula Va

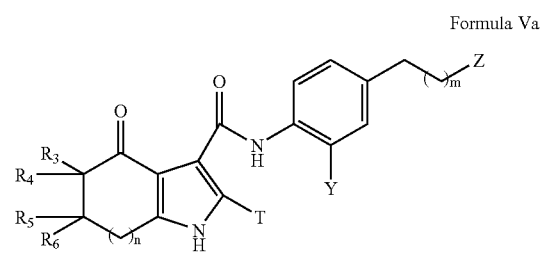

Formula Vb

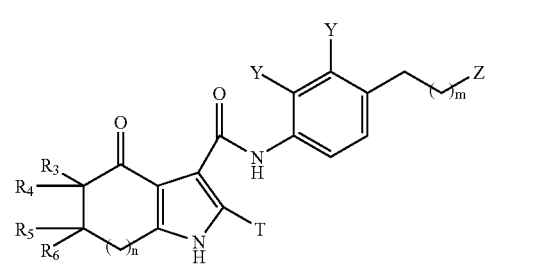

Formula Vc

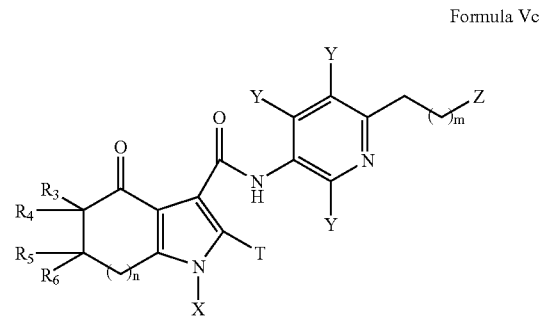

Especially preferred compounds of Formula V, Va, Vb, and Vc are compounds of wherein Z is a groups —NR$_a$R$_b$ wherein R$_a$ and R$_b$ are independently hydrogen or alkyl wherein each alkyl is independently straight, branched, or cyclic, may contain one or two double and/or triple bonds, and is unsubstituted or substituted with one or more substituents selected from: hydroxy, oxo, halogen, amino, cyano, nitro, and alkoxy; or R$_a$ and R$_b$ may be joined to form a heterocycloalkyl ring.

The present invention also encompasses compounds of Formula VI.

Formula VI

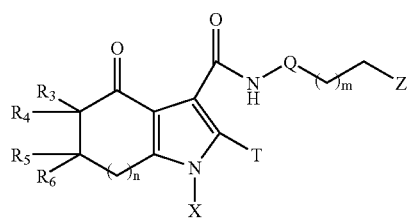

and the pharmaceutically acceptable salts thereof:

wherein n, m, $R_3$–$R_6$, X, T, and Z are defined as for Formula I;

Q is phenyl or pyridyl substituted by up to 4 groups Y, where Y is independently selected at each occurrence from hydrogen, hydroxy, halogen, $C_1$–$C_6$ alkyl, $C_1$–$C_6$ alkoxy, cyano, nitro, amino, and mono- or dialkyl($C_1$–$C_6$)amino. Particularly included as compounds of Formula VI are compounds of Formula VIa and Formula VIb (shown below).

Formula VIa

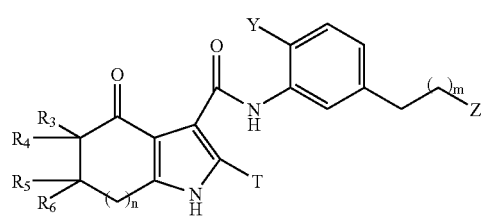

Formula VIb

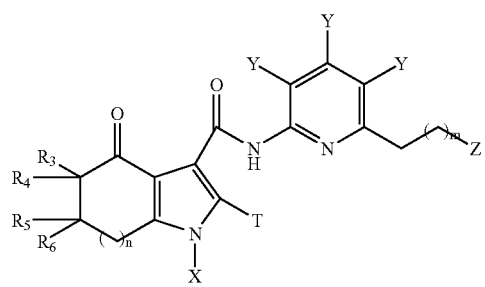

The present invention also encompasses compounds of Formula VII.

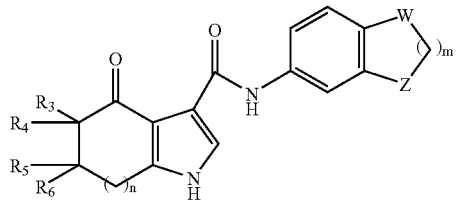

wherein W, Z, m, n, $R_3$, $R_4$, $R_5$, and $R_6$ are defined as for Formula I.

The present invention also encompasses compounds of Formula VIII.

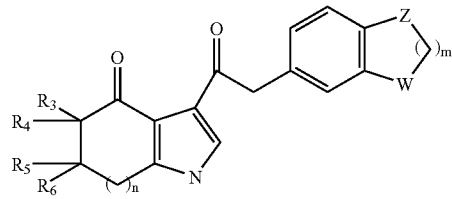

wherein W, Z, m, n, $R_3$, $R_4$, $R_5$, and $R_6$ are defined for Formula I.

The present invention also encompasses compounds of Formula IX.

IX

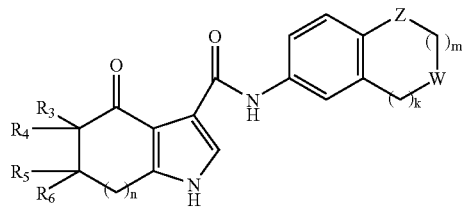

wherein W, Z, k, m, n, $R_3$, $R_4$, $R_5$, and $R_6$ are defined as for Formula I.

The present invention also encompasses compounds of Formula X.

X

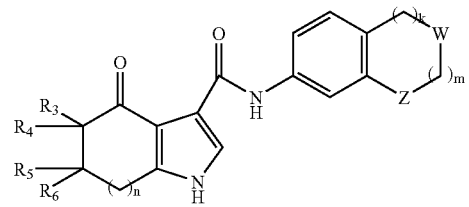

wherein W, Z, k, m, n, $R_3$, $R_4$, $R_5$, and $R_6$ are defined as for Formula I.

Preferred compounds of the invention are those where n is 1 or 2. Particularly preferred are those where X and T are both hydrogen. Thus, preferred compounds of the invention have formulas A1 or B1.

A1

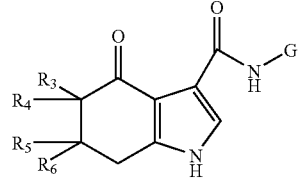

B1

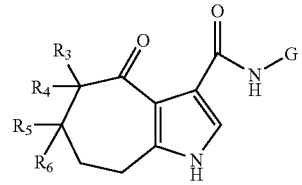

Preferred compounds of Formulas A1 and B1 are those where $R_3$, $R_4$, $R_5$ and $R_6$ are independently hydrogen or alkyl. More preferably, $R_3$, $R_4$, $R_5$ and $R_6$ are independently hydrogen, methyl, or ethyl. Even more preferably, $R_3$, $R_4$, $R_5$ and $R_6$ are hydrogen or methyl, where not more than 2 of $R_3$–$R_6$ are methyl. Particularly preferred are compounds where $R_3$ and $R_4$ are $C_1$–$C_3$ alkyl, most preferably methyl, when $R_5$ and $R_6$ are hydrogen or where $R_5$ and $R_6$ are $C_1$–$C_3$ alkyl, most preferably methyl, when $R_3$ and $R_4$ are hydrogen. Other particularly preferred compounds are those where $R_3$ is methyl and $R_4$–$R_6$ are hydrogen or $R_6$ is methyl and $R_3$–$R_5$ are hydrogen.

Preferred G substituents of the invention include the following:

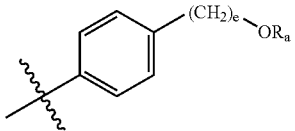

A where $R_a$ represents hydrogen or alkyl where the alkyl is optionally halogenated; and e is an integer of 1–3.

More preferred G substituents of formula A include those where e is 1, 2, or 3, and $R_a$ is hydrogen, methyl, ethyl, isopropyl, or cyclopropyl. Particularly preferred G substituents of formula A include those where e is 1, 2, or 3, and $R_a$ is hydrogen or methyl.

Another preferred G substituent is the following formula:

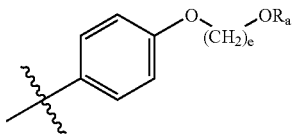

B where $R_a$ represents hydrogen or alkyl where the alkyl is optionally halogenated; and e is an integer of 1–3.

More preferred G substituents of formula B include those where e is 1, 2, or 3; and $R_a$ is hydrogen, methyl or ethyl. Particularly preferred G substituents of formula B include those where e is 1 or 2, and $R_a$ is hydrogen or methyl.

Another preferred G substituent is the following formula:

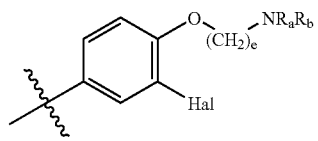

C where

Hal represents a halogen, preferably fluoro, bromo, or chloro;

$R_a$ and $R_b$ independently represent hydrogen, $C_1$–$C_6$ alkyl, $C_3$–$C_7$cycloalkyl, $C_3$–$C_7$cycloalkyl$C_1$–$C_6$alkyl where the cycloalkyl group may be substituted with halogen, $C_1$–$C_6$ alkyl, $C_1$–$C_6$ alkoxy, or mono- or di$C_1$–$C_6$ alkylamino; and e is an integer of 2–3.

Preferred compounds having formula C as the G group include those where Hal is fluoro and e is 2, 3, or 4.

More preferred G substituents of formula C include those where $R_a$ is hydrogen, methyl or ethyl; and $R_b$ is hydrogen.

Particularly preferred G substituents of formula C include those where e is 2; $R_a$ is hydrogen or methyl; and $R_b$ is hydrogen.

Another preferred G substituent is the following formula:

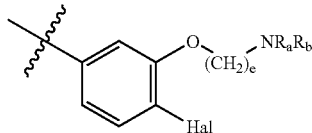

C-1 where

Hal represents a halogen, preferably fluoro, bromo, or chloro;

$R_a$ and $R_b$ independently represent hydrogen, $C_1$–$C_6$ alkyl, $C_3$–$C_7$cycloalkyl, $C_3$–$C_7$cycloalkyl$C_1$–$C_6$alkyl where the cycloalkyl group may be substituted with halogen, $C_1$–$C_6$ alkyl, $C_1$–$C_6$ alkoxy, or mono- or di$C_1$–$C_6$ alkylamino; and e is an integer of 2–3.

Preferred compounds having formula C-1 as the G group include those where Hal is fluoro and e is 2, 3, or 4.

Another preferred G substituent is the following formula:

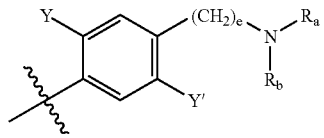

D where $R_a$ represents hydrogen, alkyl, or $C_{3-7}$ cycloalkyl, or a group of the formula:

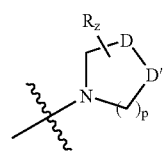

where p is 1, 2, or 3;

D and D' independently represent oxygen, $NR_y$ or $CHR_y$, provided that only one of D and D' may be $NR_y$, where each $R_y$ is hydrogen or $C_1$–$C_6$ alkyl; and $R_z$ is hydrogen or $C_1$–$C_6$ alkyl; and $R_b$ represents hydrogen, alkyl, or acyl;

Y and Y' independently represent hydrogen or halogen; and e is an integer of 1–3.

More preferred G substituents of formula D are those where Y is hydrogen or fluorine; and e is 1 or 2. Particularly preferred G substituents of formula D are those where Y is hydrogen or fluorine; e is 1 or 2; $R_a$ is hydrogen, $C_{1-3}$ alkyl, or cyclopropyl, and $R_b$ is hydrogen, methyl, or acyl. Other particularly preferred G substituents of formula D are those where Y is hydrogen and Y' is fluorine. Still other particularly preferred G groups of Formula D are those where e is 1 or 2; $R_a$ is hydrogen, $C_{1-3}$ alkyl, cyclopropyl or cyclopropylmethyl, and $R_b$ is hydrogen, methyl, or acyl.

Another preferred G substituent is the following formula:

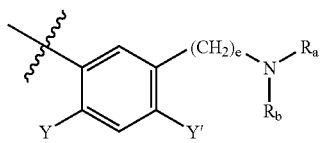
D-1 where $R_a$ represents hydrogen, alkyl, or $C_{3-7}$ cycloalkyl; and
$R_b$ represents hydrogen, alkyl, or acyl; or
$R_a$ and $R_b$ independently represent hydrogen, $C_1$–$C_6$ alkyl, $C_{3-7}$cycloalkyl$C_1$–$C_6$alkyl; and
Y and Y' independently represent hydrogen or halogen; and
e is an integer of 1–3.

More preferred G substituents of formula D are those where Y is hydrogen or fluorine; and e is 1 or 2. Particularly preferred G substituents of formula D are those where Y is hydrogen or fluorine; e is 1 or 2; $R_a$ is hydrogen, $C_{1-3}$ alkyl, or cyclopropyl, and $R_b$ is hydrogen, methyl, or acyl. Other particularly preferred G substituents of formula D are those where Y is hydrogen and Y' is fluorine. Still other particularly preferred G groups of Formula D are those where e is 1 or 2; $R_a$ is hydrogen, $C_{1-3}$ alkyl, cyclopropyl or cyclopropylmethyl, and $R_b$ is hydrogen, methyl, or acyl.

Another preferred G substituent is the following formula:

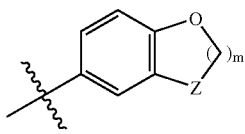
E where Z is oxygen, nitrogen, or methylene; and m is 1 or 2.

Particularly preferred G substituents of formula E are those where Z is oxygen, and m is 1 or 2. Other particularly preferred G substituents of formula E are those where Z is nitrogen, and m is 1 or 2.

Another preferred G substituent is the following formula:

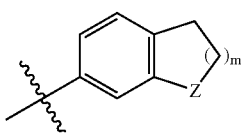
F where Z is oxygen or nitrogen; and m is 1 or 2.

Particularly preferred G substituents of formula F are those where Z is nitrogen, and m is 1 or 2.

Another preferred G substituent is the following formula:

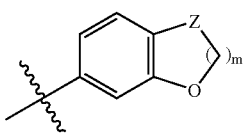
H where Z is oxygen, nitrogen, or methylene; and m is 1 or 2.

Particularly preferred G substituents of formula H are those where Z is nitrogen, and m is 1 or 2.

Another preferred G substituent is the following formula:

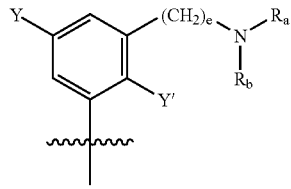
J where
$R_a$ represents hydrogen, alkyl, or $C_{3-7}$ cycloalkyl;
$R_b$ represents hydrogen, alkyl, or acyl;
Y and Y' independently represent hydrogen or halogen; and
e is an integer of 1–3.

More preferred G substituents of formula J are those where Y and Y' are independently hydrogen or fluorine; and e is 1 or 2. Particularly preferred G substituents of formula J are those where and Y' are independently hydrogen or fluorine; e is 1 or 2; $R_a$ is hydrogen, $C_{1-3}$ alkyl, or cyclopropyl, and $R_b$ is hydrogen, methyl, or acyl.

Another preferred G substituent is the following formula:

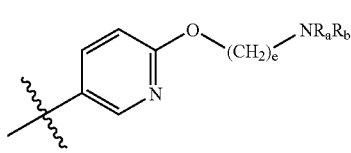
K where
$R_a$ and $R_b$ independently represent hydrogen, $C_1$–$C_6$ alkyl, $C_3$–$C_7$cycloalkyl, $C_3$–$C_7$cycloalkyl$C_1$–$C_6$alkyl where the cycloalkyl group may be substituted with halogen, $C_1$–$C_6$ alkyl, $C_1$–$C_6$ alkoxy, or mono- or di$C_1$–$C_6$ alkylamino; and
e is an integer of 2–3.

Another preferred G substituent is represented by the following formula:

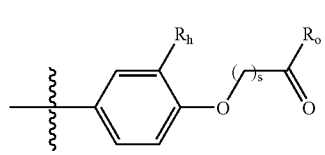
M where
$R_h$ is hydrogen, halogen, $C_1$–$C_6$alkyl, $C_1$–$C_6$alkoxy, or trifluoromethyl;
s is 0, 1, 2 or 3, and the sum of s and m is not less than 1;
$R_o$ is hydroxy, $C_1$–$C_6$alkoxy, amino, mono- or di$C_1$–$C_6$alkylamino where each alkyl is independently optionally substituted with amino, mono- or di$C_1$–$C_6$alkylamino, or
$R_o$ is a group of the formula

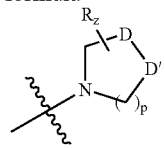

p is 1, 2, or 3;
D and D' independently represent oxygen, $NR_y$, or $CHR_y$, provided that only one of D and D' may be $NR_y$, where each $R_y$ is hydrogen or $C_1$–$C_6$ alkyl; or and
$R_z$ is hydrogen or $C_1$–$C_6$ alkyl.

Preferred M groups are those where $R_h$ is hydrogen or halogen, most preferably fluoro, and $R_o$ is a group of the formula:

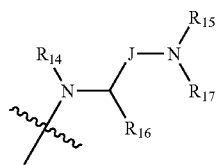

where
$R_{14}$ is hydrogen or $C_1$–$C_6$alkyl;
$R_{15}$ is hydrogen or $C_1$–$C_6$alkyl;
$R_{16}$ is hydrogen, ethyl, or methyl;
$R_{17}$ is $C_1$–$C_6$alkyl; and
J is a $C_1$–$C_4$ alkylene group, preferably methylene, ethylene, or propylene.

Particularly preferred groups of Formula M include those where s is 1 and $R_o$ is ethoxy, hydroxy, ethylamino, diethylamino, morpholinyl, piperazinyl, 4-methylpiperazinyl,

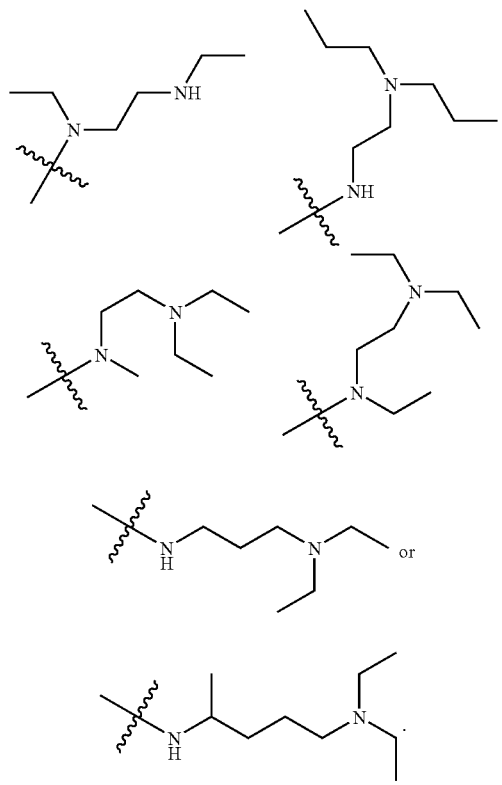

Other preferred compounds of the invention are those of Formula N-1.

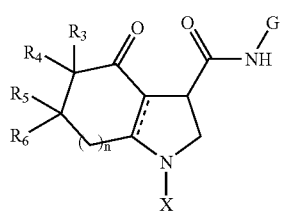

N-I wherein:
n is 1 or 2;
X is hydrogen, or alkyl;
$R_3$, $R_4$, $R_5$, and $R_6$ are the same or different and are independently selected at each occurrence from hydrogen or alkyl; and
G represents phenyl or pyridyl, each of which is substituted with a group

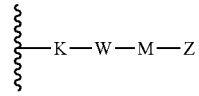

and optionally with halogen, alkyl, alkoxy, hydroxy, amino, or mono- or dialkylamino;
where
K and M independently represent a bond or $C_1$–$C_6$ alkylene;
W represents —O—, —NH—, —$NR_7$— where $R_7$ represents hydrogen or alkyl, or $C_1$–$C_3$ alkylene; and
Z is hydrogen, hydroxy, cycloalkyl(alkoxy), amino, mono- or di(alkyl$_1$)amino, or azacycloalkyl, —O(alkyl$_1$), —S(O)$_{0-2}$(alkyl$_1$), —C(=O) (alkyl$_1$), —OC(=O)(alkyl$_1$), —OC(=O)H, —C(=O)O (alkyl$_1$), —C(=O)OH, —C(=O)NH(alkyl$_1$), —C(=O)N(alkyl$_1$)$_2$, —C(=O)NH$_2$, —NHC(=O) (alkyl$_1$), —NHC(=O)H, —N(alkyl$_1$)C(=O)(alkyl$_1$), —NHS(O)$_{0-2}$(alkyl$_1$), —N(alkyl$_1$)S(O)$_{0-2}$(alkyl$_1$), —S(O)$_{0-2}$NH(alkyl$_1$), —S(O)$_{0-2}$(alkyl$_1$)N(alkyl$_1$),
wherein each alkyl$_1$ is independently straight, branched, or cyclic, may contain one or two double and/or triple bonds, and is unsubstituted or substituted with one or more substituents independently selected from hydroxy, oxo, halogen, amino, cyano, nitro, and alkoxy, or
Z is —N($R_N$)$_2$S(O)$_{0-2}$($R_S$) where
each $R_N$ is independently hydrogen or alkyl where the alkyl is straight, branched, or cyclic, may contain one or two double and/or triple bonds, and is unsubstituted or substituted with one or more substituents independently selected from hydroxy, oxo, halogen, amino, cyano, nitro, and alkoxy, and
$R_S$ is hydroxy, alkoxy, alkyl where the alkyl is optionally substituted with hydroxy, alkoxy, trifluoromethyl, halogen, amino, mono- or di-alkylamino, or
$R_s$ is heteroaryl unsubstituted or substituted with alkyl, hydroxy, alkoxy, trifluoromethyl, halogen, amino, or mono- or dialkylamino;
Z is phenyl or phenylalkyl where the phenyl portion is optionally substituted with alkyl, hydroxy, alkoxy, trifluoromethyl, halogen, amino, or mono- or di-alkylamino, or
Z is 2-, 3-, or 4-pyridyl, 1- or 2-imidazolyl, 1-, 2-, or 3-pyrrolyl, azeditinyl, norborn-2-yl, or adamantan-2-yl; each of which may be substituted on a tertiary carbon or a secondary nitrogen with $C_1$–$C_6$alkyl, or
Z represents a group of the formula:

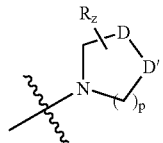

where
p is 1, 2, or 3;
D and D' independently represent oxygen, NR$_y$, or CHR$_y$, provided that only one of D and D' may be NR$_y$, where each R$_y$ is hydrogen or alkyl; and
R$_z$ is hydrogen or alkyl, or Z represents a group of the formula:

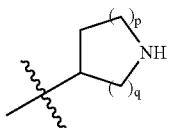

where
p is 1, 2, or 3; and
q is 0, 1, or 2; or

Z represents a group of the formula:

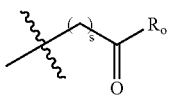

where
s is 0, 1, 2 or 3, and the sum of s and m is not less than 1;
R$_o$ is hydroxy, C$_1$–C$_6$alkoxy, amino, mono- or dialkylamino where each alkyl is independently optionally substituted with amino, mono- or dialkylamino, or
R$_o$ is a group of the formula

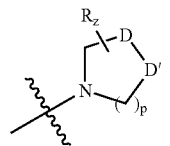

where p, D, D', and R$_z$ are as defined above.

Preferred compounds of formula N-I include those where X is hydrogen. Other preferred compounds of formula N-I are those where X is C$_1$–C$_6$ alkyl, most preferably, methyl.

More preferred compounds of N-I are those where K is a bond and W is oxygen. In other more preferred compounds of formula N-I, K is a bond and W is a bond or methylene.

Still more preferred compounds of N-I are those where M is C$_2$ or C$_3$ alkylene. In other more preferred compounds of formula N-I, M is C$_2$ or C$_3$ alkylene. In these more preferred compounds of formula N-I, G is phenyl. Alternatively, G is pyridyl in more preferred compounds of formula N-I.

In preferred compounds of formula N-I,
Z is amino, mono- or di(alkyl)amino, or azacycloalkyl, —O(alkyl), —S(O)$_{0-2}$(alkyl), —C(=O)(alkyl), —OC(=O)(alkyl), —OC(=O)H, —C(=O)O(alkyl), —C(=O)OH, —C(=O)NH(alkyl), —C(=O)N(C$_1$–C$_6$ alkyl$_1$)$_2$, —C(=O)NH$_2$, —NHC(=O)(alkyl), —NHC(=O)H, —N(alkyl)C(=O)(alkyl), —NHS(O)$_{0-2}$(alkyl), —N(alkyl)S(O)$_{0-2}$(alkyl), —S(O)$_{0-2}$NH(alkyl), —S(O)$_{0-2}$(alkyl)N(alkyl), or
Z is —N(R$_N$)$_2$SO$_2$(R$_S$) where
each R$_N$ is independently hydrogen or alkyl, and
R$_S$ is hydroxy, alkoxy, or alkyl where the alkyl is optionally substituted with hydroxy, alkoxy, trifluoromethyl, halogen, amino, or mono- or di-alkylamino, or
R$_S$ is phenyl, imidazolyl, pyridyl, pyrimidinyl, pyrrolyl, pyrazolyl, oxazolyl, isoxazolyl, thiazolyl, or isothiazolyl, each of which is optionally substituted with alkyl, hydroxy, alkoxy, trifluoromethyl, halogen, amino, or mono- or dialkylamino.

Preferred compounds of Formula I above (including all subformulae such as IIb, IIC etc), exhibit K$_i$ values of less than 100 nM at the GABA$_A$ receptor as determined by an assay of GABA$_A$ receptor binding, especially preferred compounds of Formula I-X exhibit K$_i$ values of less than 10 nM at the GABA$_A$ receptor as determined by an assay of GABA$_A$ receptor binding.

Representative compounds of the invention are shown below in Table 1.

TABLE 1

| Compound 1 | |
|---|---|
| | 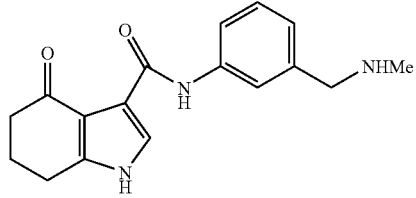 |
| Compound 2 | |
| | 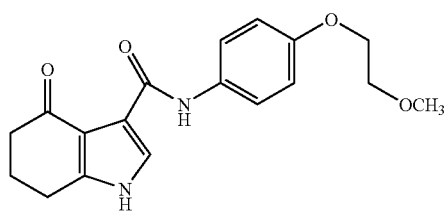 |

TABLE 1-continued
Compound 3
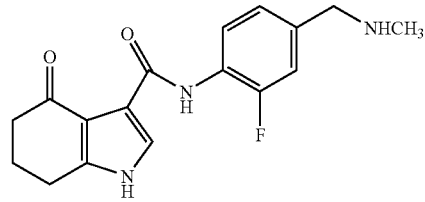
Compound 4
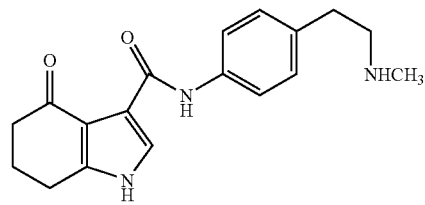
Compound 5
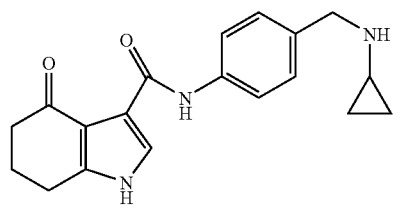
Compound 6
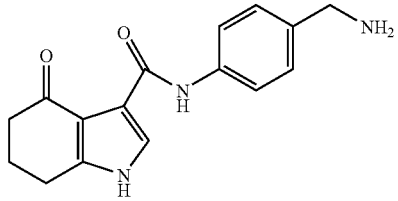
Compound 7
Compound 8
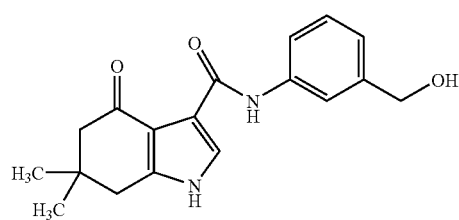
Compound 9
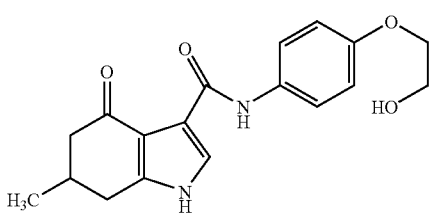

TABLE 1-continued
Compound 10
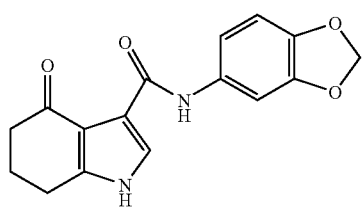
Compound 11
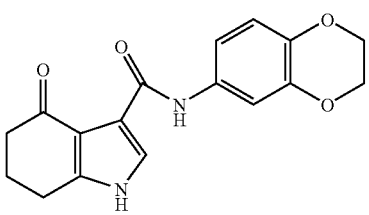
Compound 12
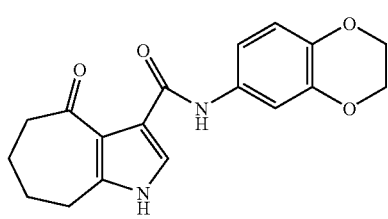
Compound 13
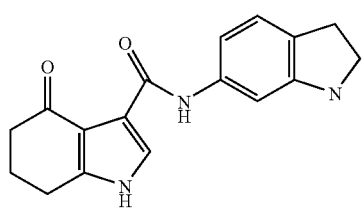
Compound 14
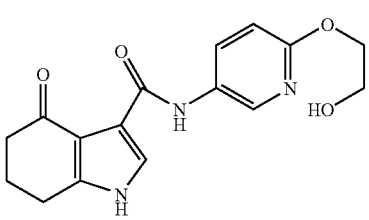
Compound 15
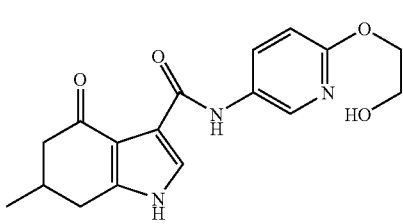
Compound 47
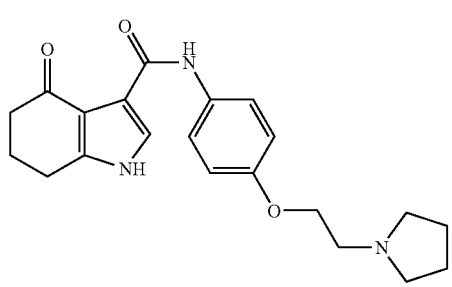

TABLE 1-continued
Compound 86
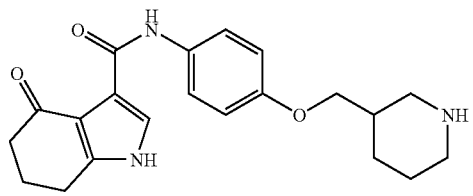
Compound 95
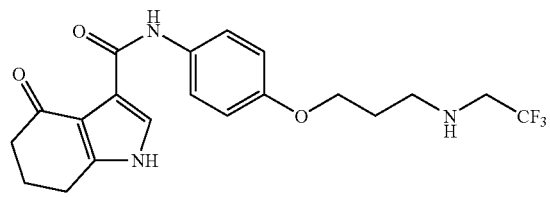
Compound 115
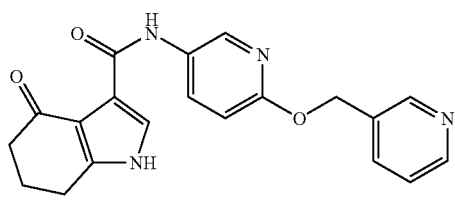
Compound 145
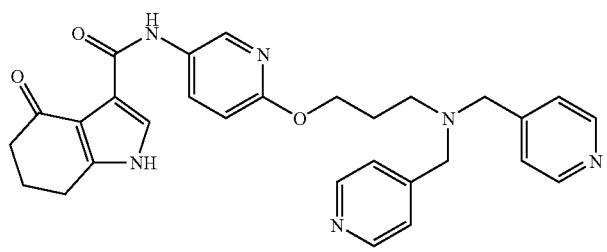
Compound 148
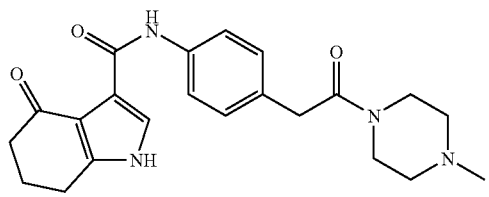
Compound 149
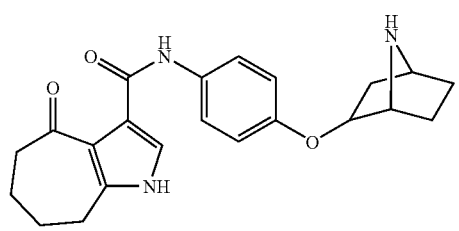
Compound 179
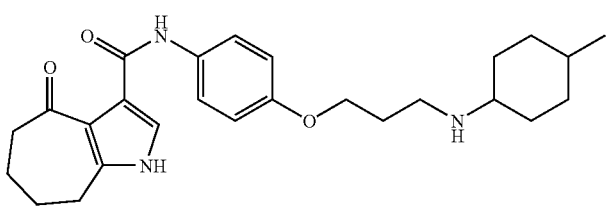

TABLE 1-continued
Compound 222
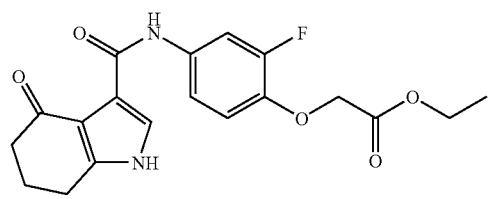
Compound 226
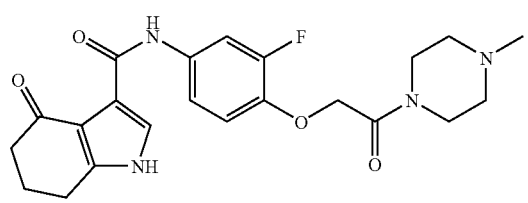
Compound 227
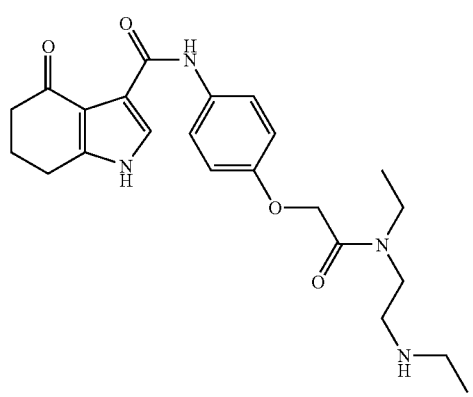
Compound 229
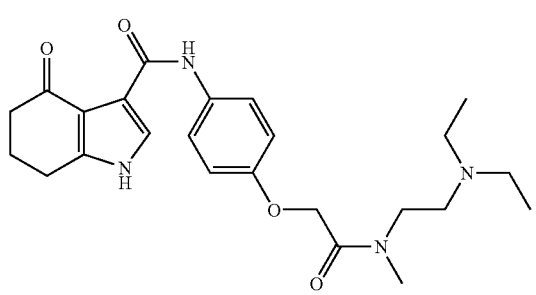
Compound 235
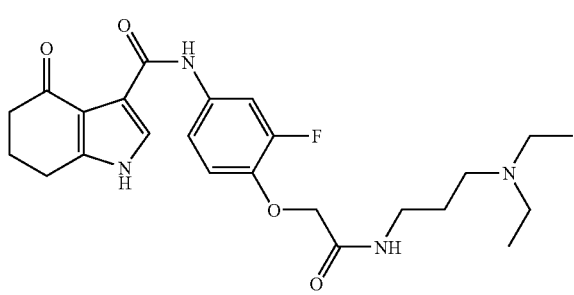

The following numbering conventions are used to identify positions on the ring systems in the compounds of the invention:

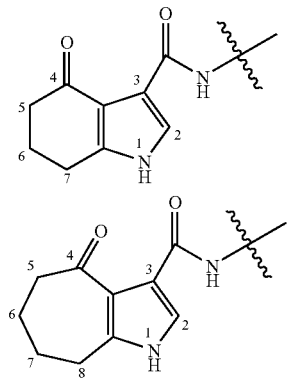

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

Representative compounds of the present invention, which are encompassed by Formula I, include, but are not limited to the compounds in Table 1 and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

This invention relates to fused pyrrolecarboxamide compounds that bind with high affinity to the benzodiazepine site of $GABA_A$ receptors, including human $GABA_A$ receptors. This invention also includes such compounds that bind with high selectivity to the benzodiazepine site of $GABA_A$ receptors, including human $GABA_A$ receptors. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorders, e.g. Attention Deficit Disorder (ADD), Attention Deficit and Hyperactivity Disorder (ADHD).

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of GABA$_A$ receptor ligands, 1,2,4-triazolo[4,3-b]pyridazines, in combination with SSRIs.

The present invention also pertains to methods of inhibiting the binding of benzodiazepine compounds, such as Ro15-1788, to the GABA$_A$ receptors which methods involve contacting a compound of the invention with cells expressing GABA$_A$ receptors, wherein the compound is present at a concentration sufficient to inhibit benzodiazepine binding to GABA$_A$ receptors in vitro. This method includes inhibiting the binding of benzodiazepine compounds to GABA$_A$ receptors in vivo, e.g., in a patient given an amount of a compound of Formula I that would be sufficient to inhibit the binding of benzodiazepine compounds to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via an GABA$_A$ receptor binding assay, such as the assay described in Example 8. The GABA$_A$ receptors used to determine in vitro binding may be obtained from a variety of sources, for example from preparations of rat cortex or from cells expressing cloned human GABA$_A$ receptors.

The present invention also pertains to methods for altering the signal-transducing activity, particulary the chloride ion conductanc of GABA$_A$ receptors, said method comprising exposing cells expressing such receptors to an effective amount of a compound of the invention. This method includes altering the signal-transducing activity of GABA$_A$ receptors in vivo, e.g., in a patient given an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 9.

The GABA$_A$ receptor ligands provided by this invention and labeled derivatives thereof are also useful as standards and reagents in determining the ability of a potential pharmaceutical to bind to the GABA$_A$ receptor.

Labeled derivatives the GABA$_A$ receptor ligands provided by this invention are also useful as radiotracers for positron emission tomography (PET) imaging or for single photon emission computerized tomography (SPECT).

Definitions

If the compounds of the present invention have asymmetric centers, then this invention includes all of the optical isomers and mixtures thereof.

In addition, compounds with carbon-carbon double bonds may occur in cis, trans, Z- and E- forms, with all isomeric forms of the compounds being included in the present invention.

A dashed line ( - - - ) in a Formula indicates an optional bond. Thus the Formula

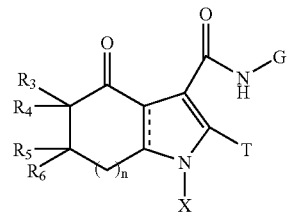

represents either

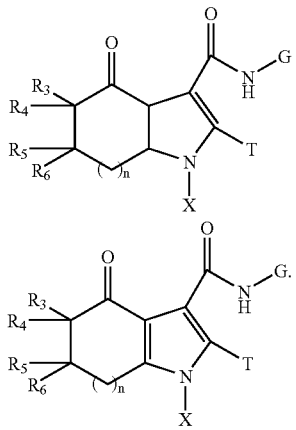

When any variable (e.g., C$_1$–C$_6$ alkyl, alkyl$_1$, R$_3$, R$_4$, R$_5$, R$_6$, X, T, G, W, Z, k, or m) occurs more than one time in Formula I, its definition on each occurrence is independent of its definition at every other occurrence.

By "alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" or "lower alkoxy" in the present invention is meant straight or branched chain alkyl group having 1–6 carbon atoms, attached to the parent molecular moiety through an oxygen atom. Examples of alkoxy groups include, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "alkenyl" is intended to include either straight or branched hydrocarbon chains containing at least one carbon-carbon double bond which may occur in any stable point along the chain. Examples of alkenyl groups include ethenyl and propenyl.

The term "alkynyl" is intended to include either a straight or branched hydrocarbon chain containing at least one carbon-carbon triple bond which may occur in any stable point along the chain, such as ethynyl and propynyl.

By "diC$_1$–C$_6$alkylamino" is meant an amino group carrying two C$_1$–C$_6$alkyl groups that are the same or different.

By "benzoxazinyl" as used herein is meant a moiety of the formula:

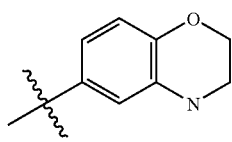

A benzoxazin-6-yl group is depicted.

By "halogen" in the present invention is meant fluorine, bromine, chlorine, and iodine.

By "2-hydroxyethoxy" is meant a group of the formula: —OCH$_2$CH$_2$OH.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl. The aryl groups of the invention are unsubstituted or may be substituted as provided herein. Examples of suitable substituents include hydroxy, halogen, $C_1$–$C_6$ alkyl, $C_1$–$C_6$ alkoxy, cyano, nitro, amino, mono- or dialkyl($C_1$–$C_6$)amino, carboxamide, and N-mono- or N,N-disubstituted carboxamide.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidinyl, imidazolyl, benzimidazolyl, furanyl, benzofuranyl, thiazolyl, thiadiazolyl, benzothiazolyl, imidazo[1,2-a]pyridinyl, isoxazolyl, oxadiazolyl, isothiazolyl, benzisothiazolyl, triazolyl, tetrazolyl, pyrrolyl, indolyl, pyrazolyl, and benzopyrazolyl. These heteroaryl groups can be unsubstituted or may be substituted as provided herein. Examples of suitable substituents include hydroxy, halogen, $C_1$–$C_6$ alkyl, $C_1$–$C_6$ alkoxy, cyano, nitro, amino, mono- or dialkyl($C_1$–$C_6$)amino, carboxamide, and N-mono- or N,N-disubstituted carboxamide.

By a 2-, 3-, or 4-pyridyl, 1- or 2-imidazolyl, 1-, 2-, or 3-pyrrolyl, or adamantane-2-yl group that is substituted on a tertiary carbon or a secondary nitrogen with $C_1$–$C_6$ alkyl is meant any such group in which a hydrogen atom is replaced with an appropriate alkyl group. By way of example, such groups include the following:

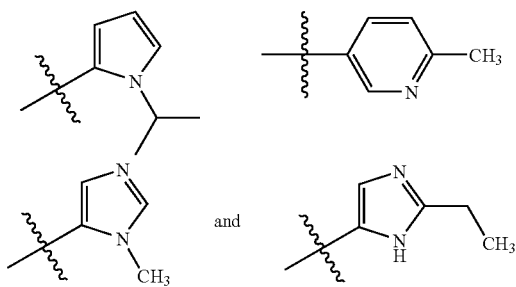

By "heterocycloalkyl" is meant a non-aromatic ring system comprising one or two rings of 4-, 5-, 6-, or 7-atoms per ring wherein at least one ring contains at least one and up to 4 heteroatoms selected from nitrogen, oxygen, or sulfur. Such heterocycloalkyl groups include, for example, tetrahydropyridyl, morpholinyl, thiomorpholinyl, pyrrolidinyl, piperazinyl, and tetrahydrofuryl. The heterocycloalkyl group can be attached to the parent molecular moiety through the heteroatom or through a carbon atom. These groups may be substituted with from one to four groups independently selected from alkyl, alkoxy, halogen, hydroxy, amino and mono- or dialkylamino groups. Preferred substituents are hydroxy, methoxy, ethoxy, chloro, fluoro, bromo, methyl and ethyl. More preferred heterocycloalkyl groups are those that are independently substituted with two of hydroxy, methoxy, ethoxy, chloro, fluoro, bromo, methyl or ethyl. Particularly preferred heterocycloalkyl groups are those that are substituted with one of hydroxy, methoxy, ethoxy, chloro, fluoro, bromo, methyl or ethyl.

By "N-alkylpiperazyl" in the invention is meant radicals of the formula:

where R is a straight or branched chain lower alkyl as defined above.

By "acyclic moiety having 3–7 carbon atoms" is meant a cytobutyl, cyclopentyl, cyclohexyl or cycloheptyl. Each of these groups may be substituted with alkyl, alkoxy, hydroxy, halogen, amino or mono- or dialkylamino. Preferred substituents are alkyl and alkoxy. Particularly preferred are alkyl with methyl and ethyl being most preferred.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formula I.

The present invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

Pharmaceutical Compositions

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcova, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

A general illustration of the preparation of compounds of Formula I in the present invention is given in Scheme I.

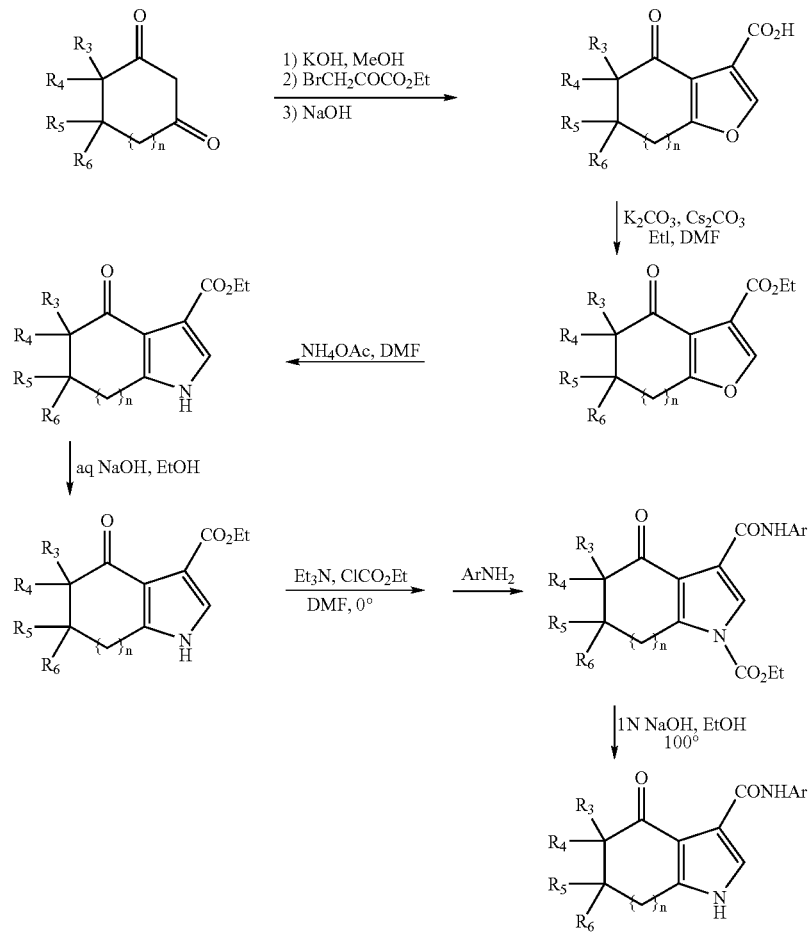

where:
Ar is

where Q, W, k, m, n, Z, $R_3$, $R_4$, $R_5$, and $R_6$ are as defined above.

Those having skill in the art will recognize that the starting materials may be varied and additional steps employed to produce compounds encompassed by the present invention, as demonstrated by the following examples.

In some cases protection of reactive functionalities may be necessary to achieve some of the above transformations. In general the need for such protecting groups will be apparent to those skilled in the art of organic synthesis as well as the conditions necessary to attach and remove such groups. Representative examples of the preparation of various protected aniline derivatives are shown in Schemes II (1), (2) and (3).

Compounds of Formula I where G is a group of, for example, formulas C, C-1, D, D-1, K or M can be made using the above outlined methods and, e.g., additional ester and amide coupling reactions. It may also be necessary to protect the indole ring nitrogen during the preparation of the compounds of the invention.

For example, compounds where $R_0$ is a dialkylamino group can be prepared from a 2-(4-nitrophenoxy)ethan-1-ol made as described above and oxidation of the hydroxy group, and subsequent formation of an acid chloride or active ester. The active ester or acid chloride may then be coupled to an appropriate amine and the resulting nitrophenyl compound used as shown in the above schemes.

Scheme III

Preparation of Substituted Aniline Intermediates

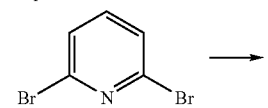

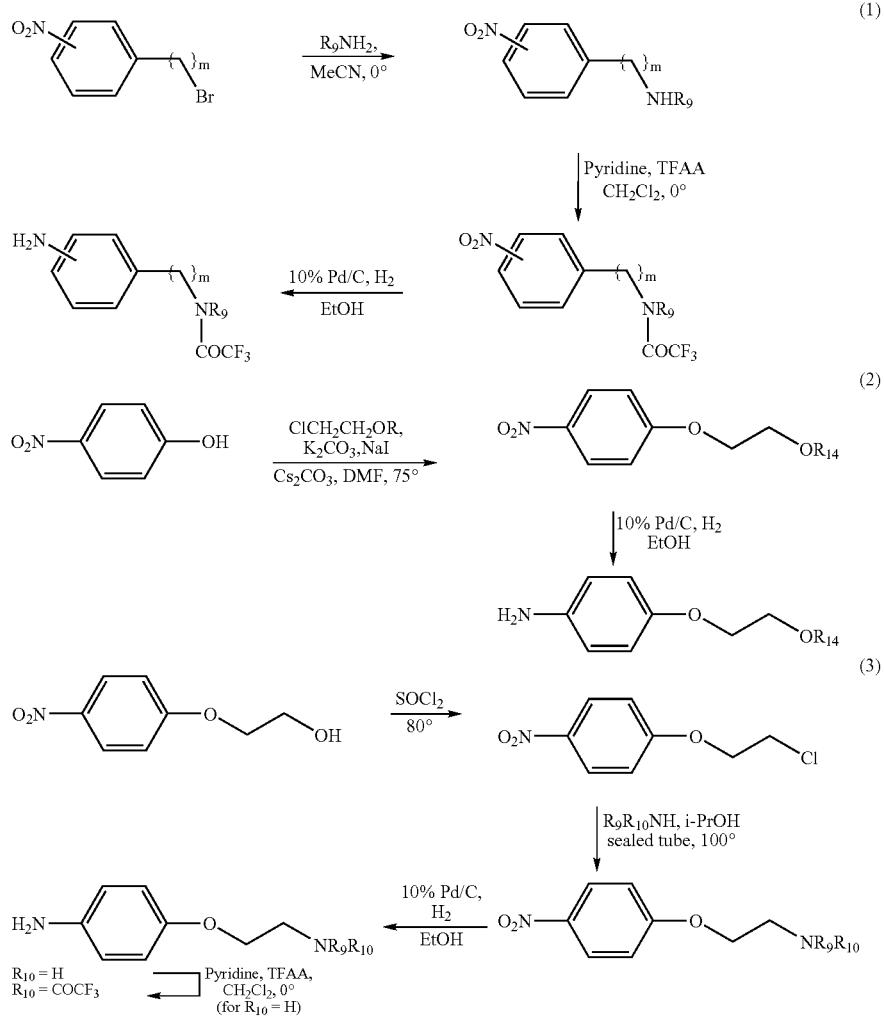

-continued

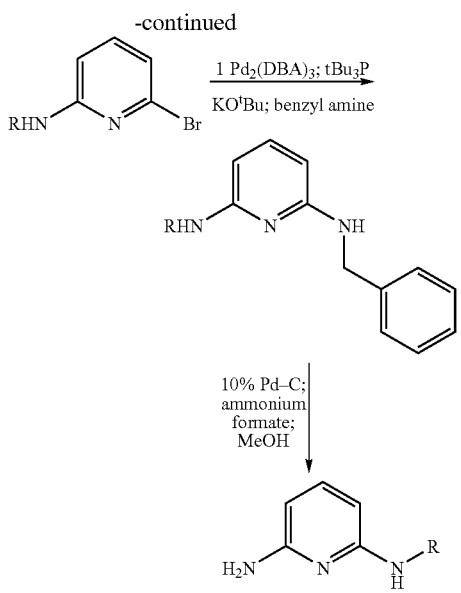

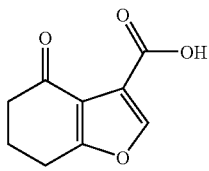

Scheme IV
Preparation of Substituted Aniline Intermediates

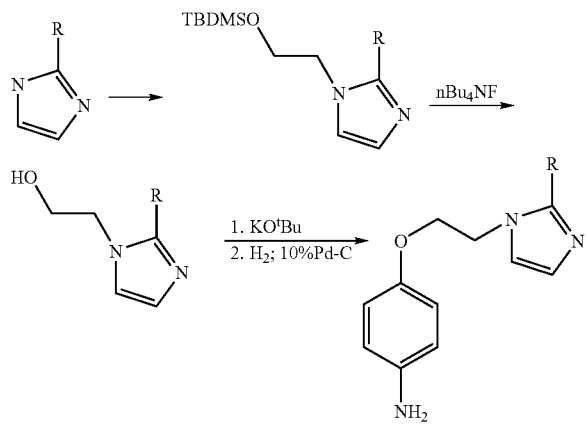

R = H, Et

Those skilled in the art will recognize that in certain instances it will be necessary to utilize different solvents or reagents to achieve some of the above transformations. Unless otherwise specified all reagents and solvent are of standard commercial grade and are used without further purification.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis.

EXAMPLES

Example 1

Preparation of Starting Materials and Intermediates

The starting materials and various intermediates may be obtained from commercial sources, prepared from commercially available organic compounds, or prepared using well known synthetic methods.

Representative examples of methods for preparing intermediates of the invention are set forth below.

1. 4-oxo-4,5,6,7-tetrahydrobenzofuran-3-carboxylic acid

4-Oxo-4,5,6,7-tetrahydrobenzofuran-3-carboxylic acid is prepared according to the following procedure. Potassium hydroxide (345 g, 6.15 mol) is dissolved in methyl alcohol (1.2 L) then cooled in an ice water bath. A solution of cyclohexanedione (714 g, 6.15 mol) in methyl alcohol (1.2 L), dissolved using gentle heat, is added dropwise to the cold, stirred KOH solution over 2 h. A solution of ethyl bromopyruvate (1200 g, 6.15 mol) in methyl alcohol (1.5 L) is then added dropwise over 3 h. The reaction mixture is allowed to reach ambient temperature and stirred an additional 14.5 h. While cooling the reaction mixture via a water bath, a solution of sodium hydroxide (492 g, 12.4 mol) in water (984 mL) is added dropwise over 2.5 h. After stirring at ambient temperature for 15.5 h, the reaction mixture is cooled in an ice water bath, 500 g of ice added, and the resulting mixture is then acidified with concentrated hydrochloric acid (ca 1 L) to pH 1. The reaction mixture is concentrated in vacuo, 1 L of ice is added, and the precipitate filtered, washed with ice water (3×200 mL), and then dried in a vacuum oven at 75° C. to afford 4-oxo-4,5,6,7-tetrahydrobenzofuran-3-carboxylic acid (560 g). m.p. 137–138° C.

2. 4-oxo-4,5,6,7-tetrahydroindole-3-carboxylate

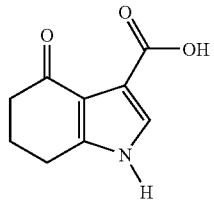

To a stirred mixture of 4-oxo-4,5,6,7-tetrahydrobenzofuran-3-carboxylic acid (640 g, 3.55 mol), potassium carbonate (1.7 kg, 10.65 mol) and cesium carbonate (100 g, 0.32 mol) in N,N-dimethylformamide (9.0 L) is added iodoethane (1250 g, 8.01 mol). The mixture is heated at 60° C. for 2 h. After cooling to ambient temperature, the mixture is filtered, the solid is rinsed with ethyl acetate, and the filtrate concentrated in vacuo. Water (2 L) is added then extracted with ethyl acetate (2×2 L); the combined organic extracts are washed with brine, dried over magnesium sulfate, filtered, and concentrated in vacuo to give ethyl 4-oxo-4,5,6,7-tetrahydrobenzofuran-3-carboxylic acid (642 g). A mixture of this ester (640 g, 3.07 mol) and ammonium acetate (426 g, 5.53 mol) in N,N-dimethylformamide (320 mL) is heated to 100° C. for 2 h. The reaction mixture is concentrated in vacuo, ice water (2.5 L) is added, and extracted with dichloromethane (2×3 L); the combined organic extracts are washed with brine, dried over magnesium sulfate, filtered, and concentrated in vacuo to give ethyl 4-oxo-4,5,6,7-tetrahydroindole-3-carboxylate (357 g). A mixture of this ester (170 g, 0.82 mol) in ethyl alcohol (250 mL) and a solution of sodium hydroxide (165 g, 4.1 mol) in water (1 L) is heated at reflux for 1 h, then cooled in an ice water bath. Concentrated hydrochloric acid (350 mL) is added dropwise, the precipitate collected by filtration, rinsed with ice water (3×), and dried in a vacuum oven at 75° C. to afford 125 g of 4-oxo-4,5,6,7-tetrahydroindole-3-carboxylate. m.p. 269–270 C.

3. 4-[N-trifluoroacetyl-(methylaminomethyl)aniline

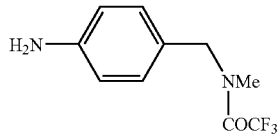

A solution of p-nitrobenzylbromide (5.40 g, 25 mmol) in acetonitrile (60 ml) is added dropwise to a stirred solution of aqueous methylamine (65 mL, 40 wt. %, 0.75 mol) in acetonitrile (50 mL) at 0°. After stirring an additional 15 minutes, the solution is poured into brine and extracted 2× with dichloromethane. The combined organic layers are washed with brine, dried over sodium sulfate, filtered, and concentrated in vacuo to give 4-(methylaminomethyl) nitrobenzene (4.04 g).

A solution of trifluoroacetic anhydride (4.46 mL, 31.6 mmol) in dichloromethane (10 mL) is added dropwise to a stirred solution of 4-(methylaminomethyl)nitrobenzene (4.04 g, 24.3 mmol) and pyridine (2.16 mL, 26.7 mmol) in dichloromethane (25 mL) at 0°. After stirring an additional 30 minutes, the solution is poured into aqueous 3.6N hydrochloric acid and extracted with dichloromethane. The organic layer is washed with brine, dried over sodium sulfate, filtered, and concentrated in vacuo to give 4-[N-trifluoroacetyl-(methylaminomethyl)]nitrobenzene (6.55 g).

Crude 4-[N-trifluoroacetyl-(methylaminomethyl)] nitrobenzene (6.55 g) is dissolved in ethyl alcohol (75 mL), added to 10% Pd/C (655 mg) in a Parr bottle and shaken under Hydrogen (50 PSI) for 4 hours. The mixture is filtered through Celite and concentrated in vacuo to give 4-[N-trifluoroacetyl-(methylaminomethyl)aniline (5.75 g).

The 3-aminoalkylanilines are prepared in a similar fashion according to the procedure generally set forth in part (1) of Scheme II above.

4. 4-amino-(N-trifluoroacetyl-2-methylaminoethoxy)benzene

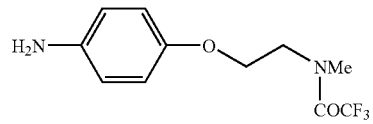

A mixture of p-nitrophenol (1.39 g, 10 mmol), 2-chloroethoxytrimethylsilane (3.2 ml, 20 mmol), potassium carbonate (4.15 g, 30 mmol), cesium carbonate (163 mg, 0.5 mmol), and sodium iodide (149 mg, 1 mmol) in N,N-dimethylformamide (10 ml) is heated at 75° for 19.5 hours. After cooling to ambient temperature, the mixture is diluted with ethyl acetate and filtered. The filtrate is washed with saturated aqueous sodium bicarbonate, then washed 2× with water, dried over magnesium sulfate, filtered, concentrated in vacuo, and purified on Silica gel (1:1 ethyl acetate/hexanes) to give 4-nitro-(2-Hydroxyethoxy)benzene (1.25 g).

4-Nitro-(2-Hydroxyethoxy)benzene (1.13 g, 6.2 mmol) in thionyl chloride (10 mL) is heated at reflux for 3 hours then concentrated in vacuo. After cooling the residue in an ice water bath, saturated aqueous sodium bicarbonate is added and the precipitate collected, rinsed with water, and dried to give 4-nitro-(2-chloroethoxy)benzene (909 mg).

A mixture of 4-nitro-(2-chloroethoxy)benzene (781 mg, 3.9 mmol) and aqueous methylamine (15 mL, 40 wt. %) in isopropyl alcohol (15 mL) is heated in a sealed tube at 100° for 4 hours. After cooling in an ice water bath, the mixture is poured into brine and extracted 2× with dichloromethane, dried over sodium sulfate, filtered, and concentrated in vacuo to give 4-nitro-(2-methylaminoethoxy)benzene (697 mg).

To a solution of 4-nitro-(2-methylaminoethoxy)benzene (766 mg, 3.9 mmol) and pyridine (0.35 mL, 4.29 mmol) in dichloromethane (5 mL) at 0° C. is added dropwise trifluoroacetic anhydride (0.72 mL, 5.08 mmol). After stirring at 0° C. for 3.5 hours, the mixture is poured into aqueous 1.2 N hydrochloric acid and extracted with dichloromethane. The organic layer is washed with saturated aqueous sodium bicarbonate then brine, dried over sodium sulfate, filtered, and concentrated in vacuo to give 4-nitro-(N-trifluoroacetyl-2-methylaminoethoxy)benzene (1.06 g). Treatment of this nitro compound with 10% Palladium on carbon in ethyl alcohol (18 mL) in a Parr bottle under Hydrogen (55 PSI) for 2.25 hours affords 4-amino-(N-trifluoroacetyl-2-methylaminoethoxy)benzene (709 mg).

Example 2

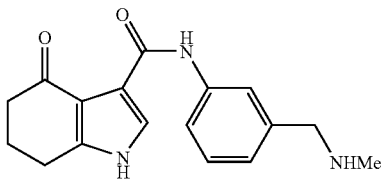

To a stirred solution of 4-oxo-4,5,6,7-tetrahydro-1H-indole-3-carboxylic acid (100 mg, 0.6 mmol) and triethylamine (0.15 mL, 1.1 mmol) in N,N-dimethylformamide (5 mL) at 0° C. is added ethyl chloroformate (0.1 mL, 1.1 mmol). After stirring an additional 1 hour, 3-(N-trifluoroacetyl-(methylaminomethyl)aniline (0.3 g, 1.3 mmol) is added. The reaction mixture is stirred for 4 hours, then poured into saturated aqueous ammonium chloride and extracted 2× with ethyl acetate. The combined organic layers are washed sequentially with brine, aqueous 2N hydrochloric acid, then brine, dried over sodium sulfate, filtered, and concentrated in vacuo. To the residue is added 15% aqueous potassium bicarbonate (5 mL) and methyl alcohol (3 mL), then heated at reflux for 3 hours. After cooling, the reaction mixture is extracted with ethyl acetate, the organic layer dried over sodium sulfate, filtered, and concentrated in vacuo to give N-[3-(methylaminomethyl)phenyl]-4-oxo-4,5,6,7-tetrahydro-1H-indole-3-carboxamide; (Compound 1) m.p. 130–132° C.

Example 3

The following compounds are prepared essentially according to the procedures described in Schemes I–IV and further illustrated in Examples 1–2:

(a) N-[3-(Methylaminomethyl)phenyl]-4-oxo-4,5,6,7-tetrahydro-1H-indole-3-carboxamide (Compound 1); mp 130–132° C.
(b) N-[4-(Hydroxyethoxy)phenyl]-4-oxo-4,5,6,7-tetrahydro-1H-indole-3-carboxamide (Compound 16); mp 245–247° C.
(c) N-[4-(Methoxyethoxy)phenyl]-4-oxo-4,5,6,7-tetrahydro-1H-indole-3-carboxamide (Compound 2).
(d) N-[-4-(3-Methylaminoethoxy)phenyl]-4-oxo-4,5,6,7-tetrahydro-1H-indole-3-carboxamide (Compound 17); mp 233–236° C.
(e) N-[4-(Methoxymethyl)phenyl]-4-oxo-4,5,6,7-tetrahydro-1H-indole-3-carboxamide (Compound 18); mp 164–165° C.
(f) N-[4-(Aminomethyl)phenyl]-4-oxo-4,5,6,7-tetrahydro-1H-indole-3-carboxamide (Compound 6); mp >200° C. (d).
(g) N-[4-(Methylaminomethyl)phenyl]-4-oxo-4,5,6,7-tetrahydro-1H-indole-3-carboxamide (Compound 19); mp 217–219° C.
(h) N-[2-Fluoro-4-(methylaminomethyl)phenyl]-4-oxo-4,5,6,7-tetrahydro-1H-indole-3-carboxamide (Compound 3); mp 186–188° C.
(i) N-{4-[N-acetyl-(methylaminomethyl)phenyl]}-4-oxo-4,5,6,7-tetrahydro-1H-indole-3-carboxamide (Compound 20); mp 204–206° C.
(j) N-[4-(Ethylaminomethyl)phenyl]-4-oxo-4,5,6,7-tetrahydro-1H-indole-3-carboxamide (Compound 21); mp 194–195° C.
(k) N-[4-(Isopropylaminomethyl)phenyl]-4-oxo-4,5,6,7-tetrahydro-1H-indole-3-carboxamide (Compound 22); mp 164–166° C.
(l) N-[4-(Cyclopropylaminomethyl)phenyl]-4-oxo-4,5,6,7-tetrahydro-1H-indole-3-carboxamide (Compound 5); mp 171–173° C.
(m) N-[4-(Dimethylaminomethyl)phenyl]-4-oxo-4,5,6,7-tetrahydro-1H-indole-3-carboxamide (Compound 23); mp 216–218° C.
(n) N-[4-(2-Aminoethyl)phenyl]-4-oxo-4,5,6,7-tetrahydro-1H-ndole-3-carboxamide (Compound 24); mp 85–90° C.
(o) N-[4-(2-Methylaminoethyl)phenyl]-4-oxo-4,5,6,7-tetrahydro-1H-indole-3-carboxamide (Compound 4); mp 197–200° C.
(p) N-[4-(Methoxymethyl)phenyl]-4-oxo-5,5-dimethyl-4,5,6,7-tetrahydro-1H-indole-3-carboxamide (Compound 25).
(q) N-[4-(Methylaminomethyl)phenyl-4-oxo-1,4,5,6,7,8-hexahydro-cycloheptal[b]pyrrole-3-carboxamide (Compound 7); mp 173–175° C.
(r) N-{4-[N-acetyl-(methylaminomethyl)phenyl]}-4-oxo-6-methyl-4,5,6,7-tetrahydro-1H-indole-3-carboxamide (Compound 26); mp 159–161° C.
(s) N-[4-(Methylaminomethyl)phenyl]-4-oxo-6-methyl-4,5,6,7-tetrahydro-1H-indole-3-carboxamide (Compound 27); mp 217–219° C.
(t) N-[4-(Hydroxymethyl)phenyl]-4-oxo-6-methyl-4,5,6,7-tetrahydro-1H-indole-3-carboxamide (Compound 28); mp 260–262° C.
(u) N-[4-(2-Hydroxyethoxy)phenyl]-4-oxo-6-methyl-4,5,6,7-tetrahydro-1H-indole-3-carboxamide (Compound 9); mp 245–247° C.
(v) N-[3-(Methylaminomethyl)phenyl]-4-oxo-6-methyl-4,5,6,7-tetrahydro-1H-indole-3-carboxamide (Compound 29); mp 172–174° C.
(w) N-[4-(2-Hydroxyethoxy)phenyl]-4-oxo-6,6-dimethyl-4,5,6,7-tetrahydro-1H-indole-3-carboxamide (Compound 30); mp 268–270° C.
(x) N-[3-(Hydroxymethyl)phenyl]-4-oxo-6,6-dimethyl-4,5,6,7-tetrahydro-1H-indole-3-carboxamide (Compound 8); mp 233–235° C.
(y) N-[4-(Hydroxymethyl)phenyl]-4-oxo-6,6-dimethyl-4,5,6,7-tetrahydro-1H-indole-3-carboxamide (Compound 31); mp 245–247° C.
(z) N-[4-(Methylaminomethyl)phenyl]-4-oxo-6,6-dimethyl-4,5,6,7-tetrahydro-1H-indole-3-carboxamide (Compound 32); mp 230–232° C.
(aa) N-(1,3-Benzodioxol-5-yl)-4-oxo-4,5,6,7-tetrahydro-1H-indole-3-carboxamide (Compound 10); mp 248–249° C.
(bb) N-(2,3-Dihydro-1,4-benzodioxin-6-yl)-4-oxo-4,5,6,7-tetrahydro-1H-indole-3-carboxamide (Compound 11); mp 254–256° C.
(cc) N-(3,4-Dihydro-2H-1,4-benzoxazin-6-yl)-4-oxo-4,5,6,7-tetrahydro-1H-indole-3-carboxamide (Compound 33); mp 216° C.
(dd) N-(2,2-Dimethyl-1,3-benzodioxol-5-yl)-4-oxo-4,5,6,7-tetrahydro-1H-indole-3-carboxamide (Compound 34).
(ee) N-(2,3-Dihydro-1H-indol-5-yl)-4-oxo-4,5,6,7-tetrahydro-1H-indole-3-carboxamide (Compound 35); mp 283–286° C.
(ff) N-(2,3-Dihydro-1H-indol-6-yl)-4-oxo-4,5,6,7-tetrahydro-1H-indole-3-carboxamide (Compound 13); mp 322–323° C.
(gg) N-(1,3-Benzodioxol-5-yl)-4-oxo-5,5-dimethyl-4,5,6,7-tetrahydro-1H-indole-3-carboxamide (Compound 36).
(hh) N-(2,3-Dihydro-1,4-benzodioxin-6-yl)-4-oxo-5,5-dimethyl-4,5,6,7-tetrahydro-1H-indole-3-carboxamide (Compound 37); mp 241–243° C.
(ii) N-(4H-1,3-Benzodioxin-7-yl)-4-oxo-5,5-dimethyl-4,5,6,7-tetrahydro-1H-indole-3-carboxamide (Compound 38); mp 251–252° C.

(jj) N-(1,3-Benzodioxol-5-yl)-4-oxo-1,4,5,6,7,8-hexahydro-cyclohepta[b]pyrrole-3-carboxamide (Compound 39); mp 210–212° C.

(kk) N-(2,3-Dihydro-1,4-benzodioxin-6-yl)-4-oxo-1,4,5,6,7,8-hexahydro-cyclohepta[b]pyrrole-3-carboxamide (Compound 12); mp 222–223° C.

(ll) N-(2,2-Dimethyl-1,3-benzodioxol-5-yl)-4-oxo-6-methyl-4,5,6,7-tetrahydro-1H-indole-3-carboxamide (Compound 40); mp 155–157° C.

(mm) N-(1,3-Benzodioxol-5-yl)-4-oxo-6-methyl-4,5,6,7-tetrahydro-1H-indole-3-carboxamide (Compound 41); mp 297–299° C.

(nn) N-(2,3-Dihydro-1,4-benzodioxin-6-yl)-4-oxo-6-methyl-4,5,6,7-tetrahydro-1H-indole-3-carboxamide (Compound 42); mp 290–292° C.

(oo) N-(1,3-Benzodioxol-5-yl)-4-oxo-6,6-dimethyl-4,5,6,7-tetrahydro-1H-indole-3-carboxamide (Compound 43); mp 245–246° C.

(pp) N-(2,3-Dihydro-1,4-benzodioxin-6-yl)-4-oxo-6,6-dimethyl-4,5,6,7-tetrahydro-1H-indole-3-carboxamide (Compound 44).

(qq) N-(4H-1,3-Benzodioxin-7-yl)-4-oxo-6,6-dimethyl-4,5,6,7-tetrahydro-1H-indole-3-carboxamide (Compound 45); mp 234–236° C.

(rr) N-[(2-Hydroxyethoxy)pyrid-5-yl]-4-oxo-6-methyl-4,5,6,7-tetrahydro-1H-indole-3-carboxamide (Compound 15); mp 221–223° C.

(ss) N-(3,4-Dihydro-2H-1,4-benzoxazin-7-yl)-4-oxo-4,5,6,7-tetrahydro-1H-indole-3-carboxamide (Compound 46).

(tt) N-[4-(2-Pyrrolidinylethoxy)phenyl]-4-oxo-4,5,6,7-tetrahydro-1H-indole-3-carboxamide; [alternate name: (4-oxo(5,6,7-trihydroindol-3-yl))-N-[4-(2-pyrrolidinylethoxy)phenyl]carboxamide] (Compound 47);

(uu) N-[3-(2-Dimethylaminoethoxy)phenyl]-4-oxo-4,5,6,7-tetrahydro-1H-indole-3-carboxamide [alternate name: (4-oxo(5,6,7-trihydroindol-3-yl))-N-[4-(2-Dimethylaminoethoxy)phenyl]carboxamide] (Compound 48);

(vv) N-[3-(2-n-Propylaminoethoxy)phenyl]-4-oxo-4,5,6,7-tetrahydro-1H-indole-3-carboxamide (Compound 49).

(ww) N-[3-(2-n-Butylaminoethoxy)phenyl]-4-oxo-4,5,6,7-tetrahydro-1H-indole-3-carboxamide (Compound 50).

(xx) N-[3-(2-Isobutylaminoethoxy)phenyl]-4-oxo-4,5,6,7-tetrahydro-1H-indole-3-carboxamide (Compound 51) (syrup).

(yy) N-[3-(2-Cyclobutylaminoethoxy)phenyl]-4-oxo-4,5,6,7-tetrahydro-1H-indole-3-carboxamide (Compound 52).

(zz) N-[3-(2-t-Butylaminoethoxy)phenyl]-4-oxo-4,5,6,7-tetrahydro-1H-indole-3-carboxamide (Compound 53).

(aaa) N-[3-(2-Cyclopropylmethylaminoethoxy)phenyl]-4-oxo-4,5,6,7-tetrahydro-1H-indole-3-carboxamide (Compound 54).

(bbb) N-{3-[2-(4-Methylcyclohexyl)aminoethoxy]phenyl}-4-oxo-4,5,6,7-tetrahydro-1H-indole-3-carboxamide (Compound 55).

(ccc) N-{3-[2-(3-Trifluoromethylbenzylamino)ethoxy]phenyl}-4-oxo-4,5,6,7-tetrahydro-1H-indole-3-carboxamide (Compound 56).

(ddd) N-{3-[3-(3-Trifluoromethylbenzylamino)propoxy]phenyl}-4-oxo-4,5,6,7-tetrahydro-1H-indole-3-carboxamide (Compound 57).

(eee) N-[4-(2-Dimethylaminoethyl)phenyl]-4-oxo-4,5,6,7-tetrahydro-1H-indole-3-carboxamide (Compound 58).

(fff) N-[4-(2-Pyrrolidin-1-ylethyl)phenyl]-4-oxo-4,5,6,7-tetrahydro-1H-indole-3-carboxamide (Compound 59); mp 184–186° C.

(ggg) N-[4-(2-Diisopropylaminoethoxy)phenyl]-4-oxo-4,5,6,7-tetrahydro-1H-indole-3-carboxamide (Compound 60).

(hhh) N-[4-(2-Methylaminoethoxy)phenyl]-4-oxo-4,5,6,7-tetrahydro-1H-indole-3-carboxamide (Compound 61).

(iii) N-[4-(2-Ethylaminoethoxy)phenyl]-4-oxo-4,5,6,7-tetrahydro-1H-indole-3-carboxamide (Compound 62); mp 140–141° C.

(jjj) N-[2-Fluoro-4-(2-ethylaminoethoxy)phenyl]-4-oxo-4,5,6,7-tetrahydro-1H-indole-3-carboxamide (Compound 63).

(kkk) N-[4-(2-n-Propylaminoethoxy)phenyl]-4-oxo-4,5,6,7-tetrahydro-1H-indole-3-carboxamide (Compound 64); mp 130–133° C.

(lll) N-[2-Fluoro-4-(2-n-propylaminoethoxy)phenyl]-4-oxo-4,5,6,7-tetrahydro-1H-indole-3-carboxamide (Compound 65).

(mmm) N-[3-Fluoro-4-(2-n-propylaminoethoxy)phenyl]-4-oxo-4,5,6,7-tetrahydro-1H-indole-3-carboxamide (Compound 66).

(mmm-a) N-[3-Fluoro-4-(2-n-propylaminoethoxy)phenyl]-4-oxo-4,5,6,7-tetrahydro-1H-indole-3-carboxamide hydrochloride (Compound 67); mp 373° C.

(nnn) N-[4-(2-Cyclopropylaminoethoxy)phenyl]-4-oxo-4,5,6,7-tetrahydro-1H-indole-3-carboxamide (Compound 68).

(ooo) N-[4-(2-Isopropylaminoethoxy)phenyl]-4-oxo-4,5,6,7-tetrahydro-1H-indole-3-carboxamide (Compound 69); mp 284–286° C.

(ppp) N-[4-(2-Cyclopropylmethylaminoethoxy)phenyl]-4-oxo-4,5,6,7-tetrahydro-1H-indole-3-carboxamide (Compound 70).

(ppp-a) N-[4-(2-Cyclopropylmethylaminoethoxy)phenyl]-4-oxo-4,5,6,7-tetrahydro-1H-indole-3-carboxamide hemifumarate (Compound 71); mp 234–234° C.

(qqq) N-[2-Fluoro-4-(2-Cyclopropylmethylaminoethoxy)phenyl]-4-oxo-4,5,6,7-tetrahydro-1H-indole-3-carboxamide (Compound 72); mp 247–250° C.

(rrr) N-[3-Fluoro-4-(2-Cyclopropylmethylaminoethoxy)phenyl]-4-oxo-4,5,6,7-tetrahydro-1H-indole-3-carboxamide (Compound 73).

(rrr-a) N-[3-Fluoro-4-(2-Cyclopropylmethylaminoethoxy)phenyl]-4-oxo-4,5,6,7-tetrahydro-1H-indole-3-carboxamide tosylate (Compound 74); mp 222° C.

(sss) N-[4-(2-Isobutylaminoethoxy)phenyl]-4-oxo-4,5,6,7-tetrahydro-1H-indole-3-carboxamide (Compound 75); dust.

(ttt) N-[2-Fluoro-4-(2-Isobutylaminoethoxy)phenyl]-4-oxo-4,5,6,7-tetrahydro-1H-indole-3-carboxamide (Compound 76); mp 152–155° C.

(uuu) N-[3-Fluoro-4-(2-Isobutylaminoethoxy)phenyl]-4-oxo-4,5,6,7-tetrahydro-1H-indole-3-carboxamide (Compound 77); mp 147–149° C.

(vvv) N-[4-(2-n-Butylaminoethoxy)phenyl]-4-oxo-4,5,6,7-tetrahydro-1H-indole-3-carboxamide (Compound 78).

(vvv-a) N-[4-(2-n-butylaminoethoxy)phenyl]-4-oxo-4,5,6,7-tetrahydro-1H-indole-3-carboxamide hydrochloride (Compound 79); mp 187–190° C.

(www) N-[3-Fluoro-4-(2-n-butylaminoethoxy)phenyl]-4-oxo-4,5,6,7-tetrahydro-1H-indole-3-carboxamide (Compound 80).

(xxx) N-[4-(2-t-Butylaminoethoxy)phenyl]-4-oxo-4,5,6,7-tetrahydro-1H-indole-3-carboxamide (Compound 81); mp 290–292° C.

(yyy) N-[3-Fluoro-4-(2-t-butylaminoethoxy)phenyl]-4-oxo-4,5,6,7-tetrahydro-1H-indole-3-carboxamide (Compound 82).

(aaaa) N-[4-(2-adamant-2-ylaminoethoxy)phenyl]-4-oxo-4,5,6,7-tetrahydro-1H-indole-3-carboxamide (Compound 83); mp 144–149° C.

(bbbb) N-{4-[(R)-Pyrrolidin-2-ylmethoxy]phenyl}-4-oxo-4,5,6,7-tetrahydro-1H-indole-3-carboxamide (Compound 84); mp 164–167–170° C.

(cccc) N-{4-[(S)-Pyrrolidin-2-ylmethoxy]phenyl}-4-oxo-4,5,6,7-tetrahydro-1H-indole-3-carboxamide (Compound 85); mp 165–167° C.

(dddd) N-[4-(Piperidin-3-ylmethoxy)phenyl]-4-oxo-4,5,6,7-tetrahydro-1H-indole-3-carboxamide (Compound 86).

(dddd-a) N-[4-(Piperidin-3-ylmethoxy)phenyl]-4-oxo-4,5,6,7-tetrahydro-1H-indole-3-carboxamide hydrochloride (Compound 87); mp 196–199° C.

(eeee) N-[4-(2-Dimethylaminoethoxy)phenyl]-4-oxo-4,5,6,7-tetrahydro-1H-indole-3-carboxamide (Compound 88); mp 201° C.

(ffff) N-[3-Fluoro-4-(2-dimethylaminoethoxy)phenyl]-4-oxo-4,5,6,7-tetrahydro-1H-indole-3-carboxamide (Compound 89); mp 203° C.

(gggg) N-[4-(2-Pyrrolidin-1-ylethoxy)phenyl]-4-oxo-4,5,6,7-tetrahydro-1H-indole-3-carboxamide (Compound 90); mp 164–168° C.

(hhhh) N-[4-(2-Imidaz-1-ylethoxy)phenyl]-4-oxo-4,5,6,7-tetrahydro-1H-indole-3-carboxamide (Compound 91); mp 226–230° C.

(iiii) N-[3-Fluoro-4-(2-moropholin-1-ylethoxy)phenyl]-4-oxo-4,5,6,7-tetrahydro-1H-indole-3-carboxamide (Compound 92); mp 200° C.

(jjjj) N-[3-Fluoro-4-(2-pyrrolidin-1-ylethoxy)phenyl]-4-oxo-4,5,6,7-tetrahydro-1H-indole-3-carboxamide (Compound 93).

(kkkk) N-[4-(2-Piperidin-2-ylethoxy)phenyl]-4-oxo-4,5,6,7-tetrahydro-1H-indole-3-carboxamide (Compound 94); mp 281–285° C.

(llll) N-{4-[3-(2,2,2,-Trifluoroethyl)aminopropoxy]phenyl}-4-oxo-4,5,6,7-tetrahydro-1H-indole-3-carboxamide (Compound 95).

(mmmm) N-[4-(3-Isopropylaminopropoxy)phenyl]-4-oxo-4,5,6,7-tetrahydro-1H-indole-3-carboxamide (Compound 96).

(nnnn) N-{4-[3-(2-Methylpropyl)aminopropoxy]phenyl}-4-oxo-4,5,6,7-tetrahydro-1H-indole-3-carboxamide (Compound 97).

(oooo) N-[4-(3-Isobutylaminopropoxy)phenyl]-4-oxo-4,5,6,7-tetrahydro-1H-indole-3-carboxamide (Compound 98).

(pppp) N-[4-(3-Cyclopropylmethylaminopropoxy)phenyl]-4-oxo-4,5,6,7-tetrahydro-1H-indole-3-carboxamide (Compound 99).

(qqqq) N-{4-[3-(3-Ethylpropyl)aminopropoxy]phenyl}-4-oxo-4,5,6,7-tetrahydro-1H-indole-3-carboxamide (Compound 100).

(rrrr) N-[4-(3-Cyclopentylaminopropoxy)phenyl]-4-oxo-4,5,6,7-tetrahydro-1H-indole-3-carboxamide (Compound 101).

(ssss) N-{4-[3-(N-Cyclopropylmethyl,N-propyl)aminopropoxy]phenyl}-4-oxo-4,5,6,7-tetrahydro-1H-indole-3-carboxamide (Compound 102).

(tttt) N-[4-(2-Methylaminoethoxy)pyrid-3-yl]-4-oxo-4,5,6,7-tetrahydro-1H-indole-3-carboxamide (Compound 103).

(uuuu) N-[4-(2-Ethylaminoethoxy)pyrid-3-yl]-4-oxo-4,5,6,7-tetrahydro-1H-indole-3-carboxamide (Compound 104).

(uuuu-a) N-[4-(2-Ethylaminoethoxy)pyrid-3-yl]-4-oxo-4,5,6,7-tetrahydro-1H-indole-3-carboxamide hydrochloride (Compound 105); mp 178–180° C.

(vvvv) N-[4-(2-n-Propylaminoethoxy)pyrid-3-yl]-4-oxo-4,5,6,7-tetrahydro-1H-indole-3-carboxamide (Compound 106).

(vvvv-a) N-[4-(2-n-Propylaminoethoxy)pyrid-3-yl]-4-oxo-4,5,6,7-tetrahydro-1H-indole-3-carboxamide hydrochloride (Compound 107); mp 177–178° C.

(wwww) N-[4-(2-Isopropylaminoethoxy)pyrid-3-yl]-4-oxo-4,5,6,7-tetrahydro-1H-indole-3-carboxamide (Compound 108).

(wwww-a) N-[4-(2-Isopropylaminoethoxy)pyrid-3-yl]-4-oxo-4,5,6,7-tetrahydro-1H-indole-3-carboxamide hydrochloride (Compound 109); mp 167–169° C.

(xxxx) N-[4-(2-n-Butylaminoethoxy)pyrid-3-yl]-4-oxo-4,5,6,7-tetrahydro-1H-indole-3-carboxamide (Compound 110).

(xxxx-a) N-[4-(2-n-Butylaminoethoxy)pyrid-3-yl]-4-oxo-4,5,6,7-tetrahydro-1H-indole-3-carboxamide hydrochloride (Compound 111); mp 157–159° C.

(yyyy) N-[4-(2-t-Butylaminoethoxy)pyrid-3-yl]-4-oxo-4,5,6,7-tetrahydro-1H-indole-3-carboxamide (Compound 112); mp 274–278° C.

(zzzz) N-[4-(2-Benzylaminoethoxy)pyrid-3-yl]-4-oxo-4,5,6,7-tetrahydro-1H-indole-3-carboxamide (Compound 113)

(zzzz-a) N-[4-(2-Benzylaminoethoxy)pyrid-3-yl]-4-oxo-4,5,6,7-tetrahydro-1H-indole-3-carboxamide hydrochloride (Compound 114); mp 143–145° C.

(aaaaa-a) N-[4-(Pyrid-3-ylmethoxy)pyrid-3-yl]-4-oxo-4,5,6,7-tetrahydro-1H-indole-3-carboxamide (Compound 115).

(aaaaa) N-[4-(Pyrid-3-ylmethoxy)pyrid-3-yl]-4-oxo-4,5,6,7-tetrahydro-1H-indole-3-carboxamide hydrochloride (Compound 116); mp 276–277° C.

(bbbbb) N-[4-(Pyrid-4-ylmethoxy)pyrid-3-yl]-4-oxo-4,5,6,7-tetrahydro-1H-indole-3-carboxamide (Compound 117).

(bbbbb-a) N-[4-(Pyrid-4-ylmethoxy)pyrid-3-yl]-4-oxo-4,5,6,7-tetrahydro-1H-indole-3-carboxamide hydrochloride (Compound 118); mp 293° C.

(ccccc) N-{4-[(R)-Pyrrolidn-2-ylmethoxy]pyrid-3-yl}-4-oxo-4,5,6,7-tetrahydro-1H-indole-3-carboxamide (Compound 119); mp 195–198° C.

(ccccc-a) N-{4-[(R)-Pyrrolidn-2-ylmethoxy]pyrid-3-yl}-4-oxo-4,5,6,7-tetrahydro-1H-indole-3-carboxamide hydrochloride (Compound 120); mp 289–291° C.

(ddddd) N-{4-[(S)-Pyrrolidn-2-ylmethoxy]pyrid-3-yl}-4-oxo-4,5,6,7-tetrahydro-1H-indole-3-carboxamide (Compound 121); mp 138–141° C.

(eeeee) N-[4-(2-Dimethylaminoethoxy)pyrid-3-yl]-4-oxo-4,5,6,7-tetrahydro-1H-indole-3-carboxamide (Compound 122); mp 163–166° C.

(fffff) N-[4-(3-Dimethylaminopropoxy)pyrid-3-yl]-4-oxo-4,5,6,7-tetrahydro-1H-indole-3-carboxamide (Compound 123); mp 247° C.

(ggggg) N-[4-(2-Pyrrolidin-1-ylethoxy)pyrid-3-yl]-4-oxo-4,5,6,7-tetrahydro-1H-indole-3-carboxamide (Compound 124)

(ggggg-a) N-[4-(2-Pyrrolidin-1-ylethoxy)pyrid-3-yl]-4-oxo-4,5,6,7-tetrahydro-1H-indole-3-carboxamide hydrochloride (Compound 125); mp 188–245° C. (d).

(hhhhh) N-[4-(2-Dimethylaminoethoxy)pyrid-3-yl]-4-oxo-4,5,6,7-tetrahydro-1H-indole-3-carboxamide (Compound 126).

(iiiii) N-{4-[2-(4-Methyl-piperazin-1-yl)ethoxy]pyrid-3-yl}-4-oxo-4,5,6,7-tetrahydro-1H-indole-3-carboxamide (Compound 127).

(jjjjj) N-{4-[2-Morpholin-1-ylethoxy]pyrid-3-yl}-4-oxo-4,5,6,7-tetrahydro-1H-indole-3-carboxamide (Compound 128).

(kkkkk) N-{4-[2-Piperidin-1-ylethoxy]pyrid-3-yl}-4-oxo-4,5,6,7-tetrahydro-1H-indole-3-carboxamide (Compound 129).

(kkkkk-a) N-{4-[2-Piperidin-1-ylethoxy]pyrid-3-yl}-4-oxo-4,5,6,7-tetrahydro-1H-indole-3-carboxamide hydrochloride (Compound 130); mp 208–211° C.

(lllll) N-{4-[(1-Methyl-pyrrolidin-3-yl)methoxy]pyrid-3-yl}-4-oxo-4,5,6,7-tetrahydro-1H-indole-3-carboxamide (Compound 131); mp 209–211° C.

(mmmmm) N-{4-[(1-Ethyl-pyrrolidin-3-yl)methoxy]pyrid-3-yl}-4-oxo-4,5,6,7-tetrahydro-1H-indole-3-carboxamide (Compound 132).

(nnnnn) N-{4-[2-(1-Methyl-pyrrolidin-2-yl)ethoxy]pyrid-3-yl}-4-oxo-4,5,6,7-tetrahydro-1H-indole-3-carboxamide (Compound 133).

(ooooo) N-{4-[2-(1-Methyl-pyrrolidin-2-yl)ethoxy]pyrid-3-yl}-4-oxo-4,5,6,7-tetrahydro-1H-indole-3-carboxamide hydrate (Compound 134).

(ppppp) N-[4-(3-n-Propylaminopropoxy)pyrid-3-yl]-4-oxo-4,5,6,7-tetrahydro-1H-indole-3-carboxamide (Compound 135).

(qqqqq) N-[4-(3-Cyclopropylmethylaminopropoxy)pyrid-3-yl]-4-oxo-4,5,6,7-tetrahydro-1H-indole-3-carboxamide (Compound 136).

(rrrrr) N-{4-[3-(2-Ethylbutyl)aminopropoxy]pyrid-3-yl}-4-oxo-4,5,6,7-tetrahydro-1H-indole-3-carboxamide (Compound 137).

(sssss) N-[4-(3-Cyclohexylaminopropoxy)pyrid-3-yl]-4-oxo-4,5,6,7-tetrahydro-1H-indole-3-carboxamide (Compound 138).

(ttttt) N-[4-(3-Cyclohexylmethylaminopropoxy)pyrid-3-yl]-4-oxo-4,5,6,7-tetrahydro-1H-indole-3-carboxamide (Compound 139).

(uuuuu) N-{4-[3-(Pyrid-4-ylmethyl)aminopropoxy]pyrid-3-yl}-4-oxo-4,5,6,7-tetrahydro-1H-indole-3-carboxamide (Compound 140).

(vvvvv) N-[4-(2-Pyrrolidin-1-ylethoxy)pyrid-3-yl]-4-oxo-4,5,6,7-tetrahydro-1H-indole-3-carboxamide (Compound 141); mp 148–150° C.

(wwwww) N-[4-(3-Di-n-propylaminopropoxy)pyrid-3-yl]-4-oxo-4,5,6,7-tetrahydro-1H-indole-3-carboxamide (Compound 142).

(xxxxx) N-{4-[3-Di(c-propylmethyl)aminopropoxy]pyrid-3-yl}-4-oxo-4,5,6,7-tetrahydro-1H-indole-3-carboxamide (Compound 143).

(yyyyy) N-{4-[3-Di(2-ethylbutyl)aminopropoxy]pyrid-3-yl}-4-oxo-4,5,6,7-tetrahydro-1H-indole-3-carboxamide (Compound 144).

(zzzzz) N-{4-[3-Di(pyrid-4-ylmethyl)aminopropoxy]pyrid-3-yl}-4-oxo-4,5,6,7-tetrahydro-1H-indole-3-carboxamide (Compound 145).

(aaaaaa) N-{4-[2-(2-Pyrrolidin-1-ylethoxy)ethoxy]pyrid-3-yl}-4-oxo-4,5,6,7-tetrahydro-1H-indole-3-carboxamide (Compound 146).

(bbbbbb) N-{4-[2-(2,2-Dimethylaminoethylamino)-2-oxoethyl]phenyl}-4-oxo-4,5,6,7-tetrahydro-1H-indole-3-carboxamide (Compound 147).

(cccccc) N-{4-[2-(4-Methylaminopiperizin-1yl)-2-oxoethyl]phenyl}-4-oxo-4,5,6,7-tetrahydro-1H-indole-3-carboxamide (Compound 148); oil.

(dddddd) N-{4-[7-azabicyclo(2.2.1)hept-2-yloxy]phenyl}-4-oxo-1,4,5,6,7,8-hexahydro-cyclohepta[b]pyrrole-3-carboxamide (Compound 149).

(eeeeee) N-[3-(2-Diethylaminoethoxy)phenyl]-4-oxo-1,4,5,6,7,8-hexahydro-cyclohepta[b]pyrrole-3-carboxamide (Compound 150).

(ffffff) N-[3-(2-Pyrrolidin-1-ylethoxy)phenyl]-4-oxo-1,4,5,6,7,8-hexahydro-cyclohepta[b]pyrrole-3-carboxamide (Compound 151).

(gggggg) N-[3-(2-Di-Isopropylaminoethoxy)phenyl]-4-oxo-1,4,5,6,7,8-hexahydro-cyclohepta[b]pyrrole-3-carboxamide (Compound 152).

(hhhhhh) N-[3-(2-n-Propylaminoethoxy)phenyl]-4-oxo-1,4,5,6,7,8-hexahydro-cyclohepta[b]pyrrole-3-carboxamide (Compound 153).

(iiiiii) N-[3-(2-n-Butylaminoethoxy)phenyl]-4-oxo-1,4,5,6,7,8-hexahydro-cyclohepta[b]pyrrole-3-carboxamide (Compound 154).

(jjjjjj) N-[3-(Methylaminopropoxy)phenyl]-4-oxo-1,4,5,6,7,8-hexahydro-cyclohepta[b]pyrrole-3-carboxamide (Compound 155).

(kkkkkk) N-{3-[3-(N-Ethyl,N-Methyl)aminopropoxy]phenyl}-4-oxo-1,4,5,6,7,8-hexahydro-cyclohepta[b]pyrrole-3-carboxamide (Compound 156).

(llllll) N-{3-[3-(N-Cyclopropylmethyl,N-n-propyl)aminopropoxy]phenyl}-4-oxo-1,4,5,6,7,8-hexahydro-cyclohepta[b]pyrrole-3-carboxamide (Compound 157).

(mmmmmm) N-[3-(Azeditinylpropoxy)phenyl]-4-oxo-1,4,5,6,7,8-hexahydro-cyclohepta[b]pyrrole-3-carboxamide (Compound 158).

(nnnnnn) N-[3-(3-Ethylaminopropoxy)phenyl]-4-oxo-1,4,5,6,7,8-hexahydro-cyclohepta[b]pyrrole-3-carboxamide (Compound 159).

(oooooo) N-{3-[3-(2,2,2-Trifluoroethyl)aminopropoxy]phenyl}-4-oxo-1,4,5,6,7,8-hexahydro-cyclohepta[b]pyrrole-3-carboxamide (Compound 160).

(pppppp) N-[3-(3-n-Propylaminopropoxy)phenyl]-4-oxo-1,4,5,6,7,8-hexahydro-cyclohepta[b]pyrrole-3-carboxamide (Compound 161).

(rrrrrr) N-[3-(3-Isopropylaminopropoxy)phenyl]-4-oxo-1,4,5,6,7,8-hexahydro-cyclohepta[b]pyrrole-3-carboxamide (Compound 163).

(ssssss) N-[3-(3-Cyclopropylaminopropoxy)phenyl]-4-oxo-1,4,5,6,7,8-hexahydro-cyclohepta[b]pyrrole-3-carboxamide (Compound 164).

(tttttt) N-[3-(3-Cyclopropylmethylaminopropoxy)phenyl]-4-oxo-1,4,5,6,7,8-hexahydro-cyclohepta[b]pyrrole-3-carboxamide (Compound 165).

(uuuuuu) N-[3-(3-Cyclobutylaminopropoxy)phenyl]-4-oxo-1,4,5,6,7,8-hexahydro-cyclohepta[b]pyrrole-3-carboxamide (Compound 166).

(vvvvvv) N-[3-(3-Cyclohexylaminopropoxy)phenyl]-4-oxo-1,4,5,6,7,8-hexahydro-cyclohepta[b]pyrrole-3-carboxamide (Compound 167).

(wwwwww) N-{3-[3-(3-Ethylpropyl)aminopropoxy]phenyl}-4-oxo-1,4,5,6,7,8-hexahydro-cyclohepta[b]pyrrole-3-carboxamide (Compound 168).

(xxxxxx) N-{3-[3-(2-Methylpropyl)aminopropoxy]phenyl}-4-oxo-1,4,5,6,7,8-hexahydro-cyclohepta[b]pyrrole-3-carboxamide (Compound 169).

(yyyyyy) N-[3-(3-Isobutylaminopropoxy)phenyl]-4-oxo-1,4,5,6,7,8-hexahydro-cyclohepta[b]pyrrole-3-carboxamide (Compound 170).

(zzzzzz) N-[3-(3-t-Butylaminopropoxy)phenyl]-4-oxo-1,4,5,6,7,8-hexahydro-cyclohepta[b]pyrrole-3-carboxamide (Compound 171).

(aaaaaaa) N-{3-[3-(2-Methylbutyl)aminopropoxy]phenyl}-4-oxo-1,4,5,6,7,8-hexahydro-cyclohepta[b]pyrrole-3-carboxamide (Compound 172).

(bbbbbbb) N-[3-(3-Isoamylaminopropoxy)phenyl]-4-oxo-1,4,5,6,7,8-hexahydro-cyclohepta[b]pyrrole-3-carboxamide (Compound 173).

(ccccccc) N-{3-[3-(4-Methylpentyl)aminopropoxy]phenyl}-4-oxo-1,4,5,6,7,8-hexahydro-cyclohepta[b]pyrrole-3-carboxamide (Compound 174).

(ddddddd) N-{3-[3-(1,1-Dimethylpropyl)aminopropoxy]phenyl}-4-oxo-1,4,5,6,7,8-hexahydro-cyclohepta[b]pyrrole-3-carboxamide (Compound 175).

(eeeeeee) N-{3-[3-(3,3,-Dimethylbutyl)aminopropoxy]phenyl}-4-oxo-1,4,5,6,7,8-hexahydro-cyclohepta[b]pyrrole-3-carboxamide (Compound 176).

(ffffff) N-{3-[3-(2,4-Dimethylpent-3-yl)aminopropoxy]phenyl}-4-oxo-1,4,5,6,7,8-hexahydro-cyclohepta[b]pyrrole-3-carboxamide (Compound 177).

(ggggggg) N-{3-[3-(4-Methylcyclohexyl)aminopropoxy]phenyl}-4-oxo-1,4,5,6,7,8-hexahydro-cyclohepta[b]pyrrole-3-carboxamide (Compound 178).

(hhhhhhh) N-{3-[3-(4-t-Butylcyclohexyl)aminopropoxy]phenyl}-4-oxo-1,4,5,6,7,8-hexahydro-cyclohepta[b]pyrrole-3-carboxamide (Compound 179).

(iiiiiii) N-{3-[3-(2,6-Dimethylcyclohexyl)aminopropoxy]phenyl}-4-oxo-1,4,5,6,7,8-hexahydro-cyclohepta[b]pyrrole-3-carboxamide (Compound 180).

(jjjjjjj) N-{3-[3-(1-Phenylethyl)aminopropoxy]phenyl}-4-oxo-1,4,5,6,7,8-hexahydro-cyclohepta[b]pyrrole-3-carboxamide (Compound 181).

(kkkkkkk) N-[3-(3-Norborn-2-ylaminopropoxy)phenyl]-4-oxo-1,4,5,6,7,8-hexahydro-cyclohepta[b]pyrrole-3-carboxamide (Compound 182).

(lllllll) N-[3-(3-Adamant-1-ylaminopropoxy)phenyl]-4-oxo-1,4,5,6,7,8-hexahydro-cyclohepta[b]pyrrole-3-carboxamide (Compound 183); mp 175–176° C.

(mmmmmmm) N-[3-(3-Norborn-2-ylmethylaminopropoxy)phenyl]-4-oxo-1,4,5,6,7,8-hexahydro-cyclohepta[b]pyrrole-3-carboxamide (Compound 184).

(nnnnnnn) N-[3-(3-Adamant-2-ylaminopropoxy)phenyl]-4-oxo-1,4,5,6,7,8-hexahydro-cyclohepta[b]pyrrole-3-carboxamide (Compound 185).

(ooooooo) N-[4-(2-Ethylaminoethoxy)phenyl]-4-oxo-1,4,5,6,7,8-hexahydro-cyclohepta[b]pyrrole-3-carboxamide (Compound 186).

(ooooooo-a) N-[4-(2-Ethylaminoethoxy)phenyl]-4-oxo-1,4,5,6,7,8-hexahydro-cyclohepta[b]pyrrole-3-carboxamide hydrochloride (Compound 187); mp 227–228° C.

(ppppppp) N-[2-Fluoro-4-(2-Ethylaminoethoxy)phenyl]-4-oxo-1,4,5,6,7,8-hexahydro-cyclohepta[b]pyrrole-3-carboxamide (Compound 188).

(qqqqqqq) N-[4-(2-n-Propylaminoethoxy)phenyl]-4-oxo-1,4,5,6,7,8-hexahydro-cyclohepta[b]pyrrole-3-carboxamide (Compound 189).

(rrrrrrr) N-[4-(2-Cyclopropylaminoethoxy)phenyl]-4-oxo-1,4,5,6,7,8-hexahydro-cyclohepta[b]pyrrole-3-carboxamide (Compound 190).

(sssssss) N-4-(2-n-Butylaminoethoxy)phenyl]-4-oxo-1,4,5,6,7,8-hexahydro-cyclohepta[b]pyrrole-3-carboxamide (Compound 191).

(ttttttt) N-[4-(3-Ethylaminopropoxy)phenyl]-4-oxo-1,4,5,6,7,8-hexahydro-cyclohepta[b]pyrrole-3-carboxamide (Compound 192).

(uuuuuuu) N-{4-[3-(1-Phenyl-1-methylethyl)aminopropoxy]phenyl}-4-oxo-1,4,5,6,7,8-hexahydro-cyclohepta[b]pyrrole-3-carboxamide (Compound 193).

(vvvvvvv) N-[4-(Pyrid-3-ylmethoxy)pyrid-3-yl]-4-oxo-1,4,5,6,7,8-hexahydro-cyclohepta[b]pyrrole-3-carboxamide (Compound 194); mp 241–243° C.

(wwwwwww) N-[4-(Pyrid-4-ylmethoxy)pyrid-3-yl]-4-oxo-1,4,5,6,7,8-hexahydro-cyclohepta[b]pyrrole-3-carboxamide (Compound 195).

(wwwwwww-a) N-[4-(Pyrid-4-ylmethoxy)pyrid-3-yl]-4-oxo-1,4,5,6,7,8-hexahydro-cyclohepta[b]pyrrole-3-carboxamide hydrochloride (Compound 196); mp 235–240° C. (d).

(xxxxxxx) N-[4-(2-Dimethylaminoethoxy)pyrid-3-yl]-4-oxo-1,4,5,6,7,8-hexahydro-cyclohepta[b]pyrrole-3-carboxamide (Compound 197).

(yyyyyyy) N-[4-(2-Diethylaminoethoxy)pyrid-3-yl]-4-oxo-1,4,5,6,7,8-hexahydro-cyclohepta[b]pyrrole-3-carboxamide (Compound 198).

(zzzzzzz) N-[4-(2-Pyrrolidin-1-ylethoxy)pyrid-3-yl]-4-oxo-1,4,5,6,7,8-hexahydro-cyclohepta[b]pyrrole-3-carboxamide (Compound 199).

(zzzzzzz-a) N-[4-(2-Pyrrolidin-1-ylethoxy)pyrid-3-yl]-4-oxo-1,4,5,6,7,8-hexahydro-cyclohepta[b]pyrrole-3-carboxamide hydrochloride (Compound 200); mp 160–162° C.

(aaaaaaaa) N-[4-(2-Piperidin-1-ylethoxy)pyrid-3-yl]-4-oxo-1,4,5,6,7,8-hexahydro-cyclohepta[b]pyrrole-3-carboxamide (Compound 201).

(bbbbbbbb) N-{4-[2-(1-Methyl-pyrrolidin-2-yl)ethoxy]pyrid-3-yl}-4-oxo-1,4,5,6,7,8-hexahydro-cyclohepta[b]pyrrole-3-carboxamide (Compound 202).

(cccccccc) N-{4-[(1-Ethyl-pyrrolidin-3-yl)methoxy]pyrid-3-yl}-4-oxo-1,4,5,6,7,8-hexahydro-cyclohepta[b]pyrrole-3-carboxamide (Compound 203); oil.

(dddddddd) N-[4-(2-Morpholin-1-ylethoxy)pyrid-3-yl]-4-oxo-1,4,5,6,7,8-hexahydro-cyclohepta[b]pyrrole-3-carboxamide (Compound 204).

(eeeeeeee) N-[4-(2-Diethylaminoethoxy)pyrid-3-yl]-4-oxo-1,4,5,6,7,8-hexahydro-cyclohepta[b]pyrrole-3-carboxamide (Compound 205).

(ffffffff) N-[4-(2-n-Propylaminoethoxy)pyrid-3-yl]-4-oxo-1,4,5,6,7,8-hexahydro-cyclohepta[b]pyrrole-3-carboxamide (Compound 206).

(ffffffff-a) N-[4-(2-n-Propylaminoethoxy)pyrid-3-yl]-4-oxo-1,4,5,6,7,8-hexahydro-cyclohepta[b]pyrrole-3-carboxamide hydrochloride (Compound 207); mp 210° C.

(gggggggg) N-[4-(2-Isopropylaminoethoxy)phenyl]-4-oxo-1,4,5,6,7,8-hexahydro-cyclohepta[b]pyrrole-3-carboxamide (Compound 208).

(hhhhhhhh) N-[4-(3-Isopropylaminoproxy)phenyl]-4-oxo-1,4,5,6,7,8-hexahydro-cyclohepta[b]pyrrole-3-carboxamide (Compound 209).

(iiiiiiii) N-[4-(3-Cyclopropylaminopropoxy)phenyl]-4-oxo-1,4,5,6,7,8-hexahydro-cyclohepta[b]pyrrole-3-carboxamide (Compound 210).

(jjjjjjjj) N-[4-(3-Cyclobutylaminopropoxy)phenyl]-4-oxo-1,4,5,6,7,8-hexahydro-cyclohepta[b]pyrrole-3-carboxamide (Compound 211).

(kkkkkkkk) N-[4-(3-Cyclopropylmethylaminopropoxy)phenyl]-4-oxo-1,4,5,6,7,8-hexahydro-cyclohepta[b]pyrrole-3-carboxamide (Compound 212).

(llllllll) N-[4-(3-Isobutylaminopropoxy)phenyl]-4-oxo-1,4,5,6,7,8-hexahydro-cyclohepta[b]pyrrole-3-carboxamide (Compound 213).

(mmmmmmmm) N-{4-[3-(2,2-Dimethylpropyl)aminopropoxy]phenyl}-4-oxo-1,4,5,6,7,8-hexahydro-cyclohepta[b]pyrrole-3-carboxamide (Compound 214).

(nnnnnnnn) N-{4-[3-(3-Ethylpropyl)aminopropoxy]phenyl}-4-oxo-1,4,5,6,7,8-hexahydro-cyclohepta[b]pyrrole-3-carboxamide (Compound 215).

(oooooooo) N-{4-[3-(2-Methylbutyl)aminopropoxy]phenyl}-4-oxo-1,4,5,6,7,8-hexahydro-cyclohepta[b]pyrrole-3-carboxamide (Compound 216).

(pppppppp) N-{4-[3-(2-Methylpropyl)aminopropoxy]phenyl}-4-oxo-1,4,5,6,7,8-hexahydro-cyclohepta[b]pyrrole-3-carboxamide (Compound 217).

(qqqqqqqq) N-[4-(3-i-Pentylaminopropoxy)phenyl]-4-oxo-1,4,5,6,7,8-hexahydro-cyclohepta[b]pyrrole-3-carboxamide (Compound 218).

(rrrrrrrr) N-[4-(3-Cyclohexylaminopropoxy)phenyl]-4-oxo-1,4,5,6,7,8-hexahydro-cyclohepta[b]pyrrole-3-carboxamide (Compound 219).

(ssssssss) N-{4-[3-(N-Cyclopropylmethyl,N-n-propyl)aminopropoxy]phenyl}-4-oxo-1,4,5,6,7,8-hexahydro-cyclohepta[b]pyrrole-3-carboxamide (Compound 220).

(tttttttt) N-[4-(3-Indan-2-ylaminopropoxy)phenyl]-4-oxo-1,4,5,6,7,8-hexahydro-cyclohepta[b]pyrrole-3-carboxamide (Compound 221).

(uuuuuuuu) N-[3-Fluoro-4-(2-ethoxy-2-oxoethoxy)phenyl]-4-oxo-4,5,6,7-tetrahydro-1H-indole-3-carboxamide (Compound 222); mp 192–196° C.

(vvvvvvvv) N-[3-Fluoro-4-(2-hydroxy-2-oxoethoxy)phenyl]-4-oxo-4,5,6,7-tetrahydro-1H-indole-3-carboxamide (Compound 223); mp 246–248° C.

(wwwwwwww) N-[3-Fluoro-4-(2-ethylamino-2-oxoethoxy)phenyl]-4-oxo-4,5,6,7-tetrahydro-1H-indole-3-carboxamide (Compound 224).

(xxxxxxxx) N-[3-Fluoro-4-(2-diethylamino-2-oxoethoxy)phenyl]-4-oxo-4,5,6,7-tetrahydro-1H-indole-3-carboxamide (Compound 225); mp 193–196° C.

(yyyyyyyy) N-{3-Fluoro-4-[2-(4-methylpiperizin-1-yl)-2-oxoethoxy]phenyl}-4-oxo-4,5,6,7-tetrahydro-1H-indole-3-carboxamide (Compound 226).

(zzzzzzzz) N-ethyl-N-[2-(ethylamino)ethyl]-2-{4-[(4-oxo-(4,5,6,7-tetrahydroindol-3-yl))carbonylamino]phenoxy}acetamide (Compound 227).

(aaaaaaaaa) N-[2-(dipropylamino)ethyl]-2-{4-[(4-oxo-(4,5,6,7-tetrahydroindol-3-yl))carbonylamino]phenoxy}acetamide (Compound 228); mp 148–150° C.

(bbbbbbbb) N-[2-(diethylamino)ethyl]-N-methyl-2-{4-[(4-oxo-(4,5,6,7-tetrahydroindol-3-yl))carbonylamino]phenoxy}acetamide (Compound 229); mp 220–228° C.

(cccccccc) N-[2-(diethylamino)ethyl]-N-ethyl-2-{4-[(4-oxo-(4,5,6,7-tetrahydroindol-3-yl))carbonylamino]phenoxy}acetamide (Compound 230); mp 165–167° C.

(dddddddd) N-[4-(2-morpholin-4-yl-2-oxoethoxy)phenyl](4-oxo-(4,5,6,7-tetrahydroindol-3-yl))carboxamide (Compound 231).

(eeeeeeee) N-[3-fluoro-4-(2-morpholin-4-yl-2-oxoethoxy)phenyl](4-oxo-(4,5,6,7-tetrahydroindol-3-yl))carboxamide (Compound 232); mp 110° C.

(ffffffff) (4-oxo-(4,5,6,7-trihydroindol-3-yl))-N-[4-(2-oxo-2-piperazinylethoxy)phenyl]carboxamide (Compound 233)

(gggggggg) N-[3-(diethylamino)propyl]-2-{4-[(4-oxo-(4,5,6,7-tetrahydroindol-3-yl))carbonylamino]phenoxy}acetamide (Compound 234)

(hhhhhhhh) N-[3-(diethylamino)propyl]-2-{2-fluoro-4-[(4-oxo-(4,5,6,7-tetrahydroindol-3-yl))carbonylamino]phenoxy}acetamide (Compound 235).

(iiiiiiii) N-[4-(diethylamino)-1-methylbutyl]-2-{4-[(4-oxo-(4,5,6,7-tetrahydroindol-3-yl))carbonylamino]phenoxy}acetamide (Compound 236).

(jjjjjjjj) N-[4-(diethylamino)-1-methylbutyl]-2-{2-fluoro-4-[(4-oxo-(4,5,6,7-tetrahydroindol-3-yl))carbonylamino]phenoxy}acetamide (Compound 237).

Example 4

The compounds shown in Tables I and II were prepared using methods similar to those given in Schemes I–IV and further illustrated by Examples 1 and 2.

TABLE I

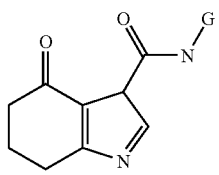

| Cmd # | Name | G | Spectral Data |
| --- | --- | --- | --- |
| 238 | N-{4-(2-(ethyl-methanesulfonyl-amino)-ethoxy]phenyl}-4-oxo-4,5,6,7-tetrahydro-1H-indole-3-carboxamide | | LRMS calcd 419 found [M + 1] |
| 239 | N-[4-(3-methanesulfonyl-propoxy)phenyl]-4-oxo-4,5,6,7-tetrahydro-1H-indole-3-carboxamide | | LRMS calcd 390 found [M + 1] 391 |
| 240 | N-4-{4-(2-(ethanesulfonyl-ethyl-amino)ethoxy]-phenyl}-oxo-4,5,6,7-tetrahydro-1H-indole-3-carboxamide | | LRMS calcd 433 found [M + 1] 434 |

TABLE I-continued

| Cmd # | Name | G | Spectral Data |
|---|---|---|---|
| 241 | N-(4-{2-[ethyl-(propane-1-sulfonyl)amino]ethoxy}phenyl)-4-oxo-4,5,6,7-tetrahydro-1H-indole-3-carboxamide | | LRMS calcd 447 found [M + 1] 448 |
| 242 | N-(4-{2-[ethyl-(thiophene-3-sulfonyl)amino]ethoxy}phenyl)-4-oxo-4,5,6,7-tetrahydro-1H-indole-3-carboxamide | | LRMS calcd 504 found [M + 1] 505 |
| 243 | N-{6-[2-(ethyl-methanesulfonyl-amino)ethoxy]pyridin-3-yl}-4-oxo-4,5,6,7-tetrahydro-1H-indole-3-carboxamide | | LRMS calcd 420 found [M + 1] 421 |
| 244 | N-[6-(1-benzyl-1H-imidazol-2-ylmethoxy)-pyridin-3-yl]-4-oxo-4,5,6,7-tetrahydro-1H-indole-3-carboxamide | | LRMS calcd 441 found [M + 1] 442 |
| 245 | N-[2-(2-aminoethoxy)pyridin-3-yl]-4-oxo-4,5,6,7-tetrahydro-1H-indole-3-carboxamide | | LRMS calcd 314 found [M + 1] 315 |

TABLE I-continued

| Cmd # | Name | G | Spectral Data |
|---|---|---|---|
| 246 | N-[6-(2-ethanesulfonylamino-ethoxy)pyridin-3-yl]-4-oxo-4,5,6,7-tetrahydro-1H-indole-3-carboxamide | | LRMS calcd 406 found [M + 1] 407 |
| 247 | N-[6-(2-methanesulfonylamino-ethoxy)-pyridin-3-yl]-4-oxo-4,5,6,7-tetrahydro-1H-indole-3-carboxamide | | LRMS calcd 392 found [M + 1] 393 |
| 248 | N-[4-(2-methanesulfonylamino-ethoxy)phenyl]-4-oxo-4,5,6,7-tetrahydro-1H-indole-3-carboxamide | | LRMS calcd 391 found [M + 1] 392 |
| 249 | N-4-Oxo-4,5,6,7-tetrahydro-1H-indole-3-carboxylic acid[2-(2-methanesulfonylamino-ethoxy)-pyridin-3-yl]-amide | | LRMS calcd 392 found [M + 1] 393 |
| 250 | N-{2-[2-(thiophene-2-sulfonylamino)ethoxy]pyridin-3-yl}-4-oxo-4,5,6,7-tetrahydro-1H-indole-3-carboxamide | | LRMS calcd 460 found [M + 1] 461 |
| 251 | N-{6-[(pyridin-2-ylmethyl)-amino]-pyridin-3-yl}-4-oxo-4,5,6,7-tetrahydro-1H-indole-3-carboxamide | | LRMS calcd 361 found [M + 1] 362 |

TABLE I-continued

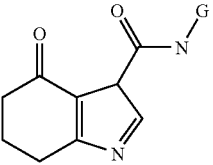

| Cmd # | Name | G | Spectral Data |
|---|---|---|---|
| 252 | N-{6-[(pyridin-3-ylmethyl)-amino]-pyridin-3-yl}-4-oxo-4,5,6,7-tetrahydro-1H-indole-3-carboxamide | 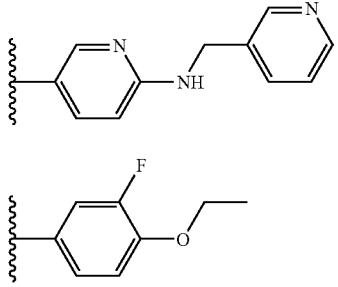 | LRMS calcd 361 found [M + 1] 362 |
| 253 | N-(4-ethoxy-3-fluoro-phenyl)-4-oxo-4,5,6,7-tetrahydro-1H-indole-3-carboxamide | 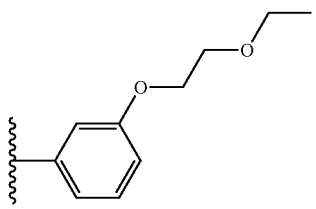 | LRMS calcd 316 found [M + 1] 317 |
| 254 | N-acid[3-(2-ethoxy-ethoxy)-phenyl]-4-Oxo-4,5,6,7-tetrahydro-1H-indole-3-carboxamide | 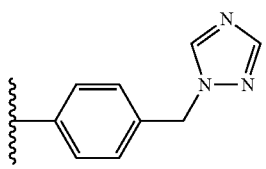 | LRMS calcd 342 found [M + 1] 343 |
| 255 | N-(4-[1,2,4]triazol-1-ylmethyl-phenyl)-4-oxo-4,5,6,7-tetrahydro-1H-indole-3-carboxamide | 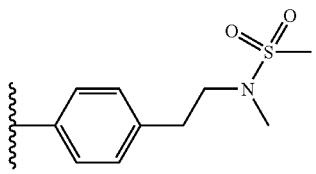 | LRMS calcd 335 found [M + 1] 336 |
| 256 | N-{4-[2-(methanesulfonyl-methyl-amino)-ethyl]-phenyl}-4-oxo-4,5,6,7-tetrahydro-1H-indole-3-carboxamide | 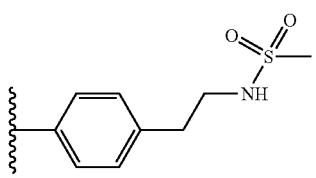 | LRMS calcd 389 found [M + 1] 390 |
| 257 | N-[4-(2-methanesulfonylamino-ethyl)-phenyl]-4-oxo-4,5,6,7-tetrahydro-1H-indole-3-carboxamide | 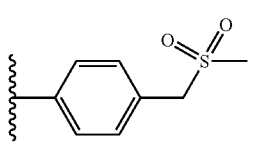 | LRMS calcd 375 found [M + 1] 378 |
| 258 | N-(4-methanesulfonylmethyl-phenyl)-4-oxo-4,5,6,7-tetrahydro-1H-indole-3-carboxamide | | LRMS calcd 346 found [M + 1] 347 |
| 259 | N-[4-(4-hydroxymethyl-imidazol-1-yl)-phenyl]-4-oxo-4,5,6,7-tetrahydro-1H-indole-3-carboxamide | 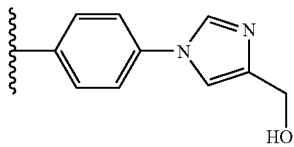 | LRMS calcd 350 found [M + 1] 351 |

TABLE I-continued

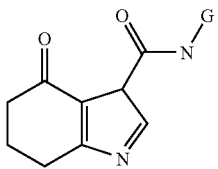

| Cmd # | Name | G | Spectral Data |
|---|---|---|---|
| 260 | N-[4-(2-methanesulfonyl-ethyl)-phenyl]-4-oxo-4,5,6,7-tetrahydro-1H-indole-3-carboxamide | | LRMS calcd 360 found [M + 1] 361 |
| 261 | (2-{4-[(4-Oxo-4,5,6,7-tetrahydro-1H-indole-3-carbonyl)-amino]-phenyl}-ethyl)-carbamic acid tert-butyl ester | | LRMS calcd 397 found [M + 1] 398 |
| 262 | N-[4-(2-imidazol-1-yl-ethyl)-phenyl]-4-oxo-4,5,6,7-tetrahydro-1H-indole-3-carboxylic acid amide | | LRMS calcd 348 found [M + 1] 349 |
| 263 | N-{4-[2-(thiophene-2-sulfonylamino)-ethyl]-phenyl}-4-oxo-4,5,6,7-tetrahydro-1H-indole-3-carboxamide | | LRMS calcd 443 found [M + 1] 444 |
| 264 | N-[4-(2-ethanesulfonylamino-ethyl)-phenyl]-4-oxo-4,5,6,7-tetrahydro-1H-indole-3-carboxamide | | LRMS calcd 389 found [M + 1] 390 |
| 265 | N-{4-[2-(propane-1-sulfonylamino)ethyl]phenyl}-4-oxo-4,5,6,7-tetrahydro-1H-indole-3-carboxamide | | LRMS calcd 403 found [M + 1] 404 |
| 266 | N-(5-ethoxy-pyridin-2-yl)-4-oxo-4,5,6,7-tetrahydro-1H-indole-3-carboxamide | | LRMS calcd 378 found [M + 1] 379 |

TABLE I-continued

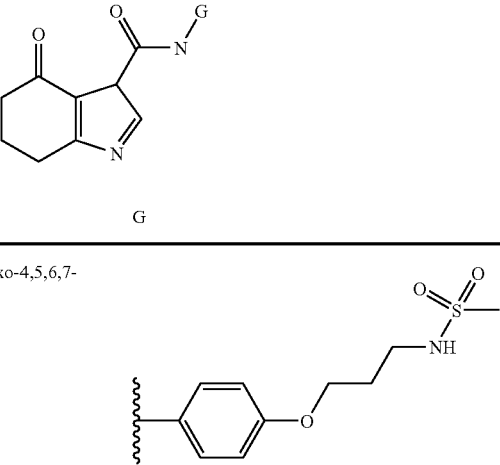

| Cmd # | Name | G | Spectral Data |
|---|---|---|---|
| 267 | N-[4-(3-methanesulfonylamino-propoxy)-phenyl]-4-oxo-4,5,6,7-tetrahydro-1H-indole-3-carboxamide | 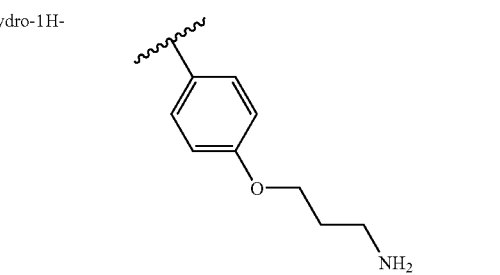 | LRMS calcd 405 found [M + 1] 406 |
| 268 | N-[4-(3-amino-propoxy)-phenyl]-4-oxo-4,5,6,7-tetrahydro-1H-indole-3-carboxamide | 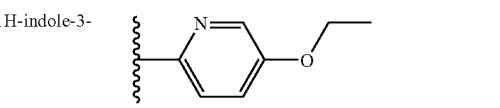 | LRMS calcd 327 found [M + 1] 328 |
| 269 | N-(5-propoxy-pyridin-2-yl)-4-oxo-4,5,6,7-tetrahydro-1H-indole-3-carboxamide | 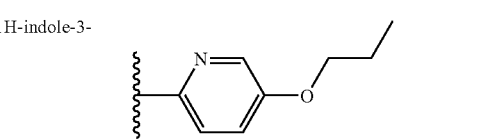 | LRMS calcd 299 found [M + 1] 300 |
| 270 | N-(5-propoxy-pyridin-2-yl)-4-oxo-4,5,6,7-tetrahydro-1H-indole-3-carboxamide | 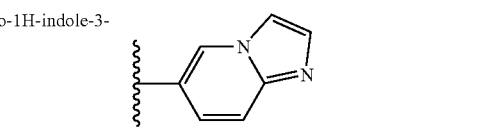 | LRMS calcd 313 found [M + 1] 314 |
| 271 | N-imidazo[1,2-a]pyridin-6-yl-4-Oxo-4,5,6,7-tetrahydro-1H-indole-3-carboxamide | 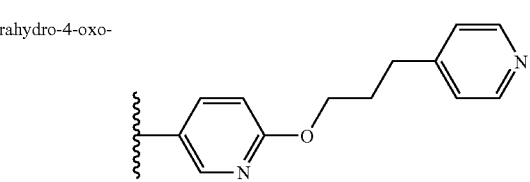 | LRMS calcd 294 found [M + 1] 295 |
| 272 | N-(6-(3-(4-pyridinyl)propoxy)-3-pyridinyl)-4,5,6,7-tetrahydro-4-oxo-1H-indole-3-carboxamide | 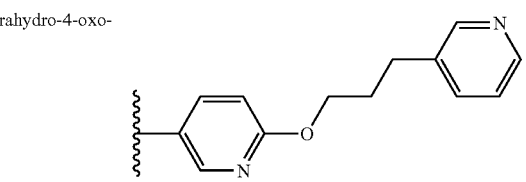 | electrospray mass spectrum: m/z 391 [M + 1] |
| 273 | N-(6-(3-(3-pyridinyl)propoxy)-3-pyridinyl)-4,5,6,7-tetrahydro-4-oxo-1H-indole-3-carboxamide | | electrospray mass spectrum: m/z 391 [M + 1] |

TABLE I-continued

| Cmd # | Name | G | Spectral Data |
|---|---|---|---|
| 274 | N-(6-(3-(2-pyridinyl)propoxy)-3-pyridinyl)-4,5,6,7-tetrahydro-4-oxo-1H-indole-3-carboxamide | | electrospray mass spectrum: m/z 391 [M + 1] |
| 275 | N-(6-(2-(2-pyridinyl)ethoxy)-3-pyridinyl)-4,5,6,7-tetrahydro-4-oxo-1H-indole-3-carboxamide | | electrospray mass spectrum: m/z 375 [M − 1] |
| 276 | N-[2-(ethylamino)pyrid-5-yl]-4-oxo-4,5,6,7-tetrahydro-1H-indole-3-carboxamide | | M.W. 298.348; MS (M + 1) 299 |
| 277 | N-[2-(methylamino)pyrid-5-yl]-4-oxo-4,5,6,7-tetrahydro-1H-indole-3-carboxamide | | M.W. 284.321; MS (M + 1) 285. |
| 278 | N-{2-[2-(pyrrolidin-1-yl)ethylamino]pyrid-5-yl}-4-oxo-4,5,6,7-tetrahydro-1H-indole-3-carboxamide | | M.W. 298.348; MS (M + 1) 299. |
| 279 | N-[2-(propylamino)pyrid-5-yl]-4-oxo-4,5,6,7-tetrahydro-1H-indole-3-carboxamide | | M.W. 312.375; MS (M + 1) 313 |
| 280 | N-{2-[(2-methoxyethyl)amino]pyrid-5-yl}-4-oxo-4,5,6,7-tetrahydro-1H-indole-3-carboxamide | | M.W. 328.375; MS (M + 1) 329 |
| 281 | N-[2-(butylamino)pyrid-5-yl]-4-oxo-4,5,6,7-tetrahydro-1H-indole-3-carboxamide | | M.W. 326.402; MS (M + 1) 327. |
| 282 | N-(6-ethoxypyridazin-3-yl)-4-oxo-4,5,6,7-tetrahydro-1H-indole-3-carboxamide | | M.W. 300.321; MS (M + 1) 301 |

TABLE I-continued

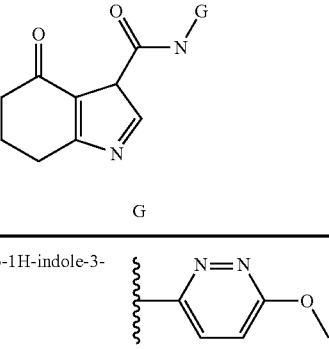

| Cmd # | Name | G | Spectral Data |
|---|---|---|---|
| 283 | N-(6-methoxypyridazin-3-yl)-4-oxo-4,5,6,7-tetrahydro-1H-indole-3-carboxamide | 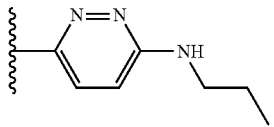 | M.W. 286.294; MS (M + 1) 287. |
| 284 | N-[6-(propylamino)pyridazin-3-yl]-4-oxo-4,5,6,7-tetrahydro-1H-indole-3-carboxamide | 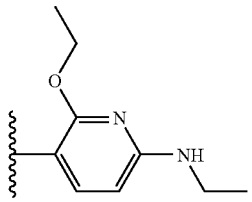 | M.W. 313.363; MS (M + 1) 314. |
| 285 | N-[2-ethoxy-6-(ethylamino)pyrid-3-yl]-4-oxo-4,5,6,7-tetrahydro-1H-indole-3-carboxamide | 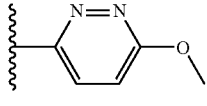 | M.W. 300.321; MS (M + 1) 301. |
| 286 | N-{2-[N-methyl(ethylamino)]pyrid-5-yl}-1-methyl-4-oxo-4,5,6,7-tetrahydro-1H-indole-3-carboxamide | 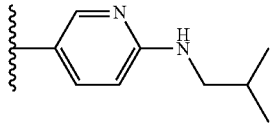 | M.W. 286.294; MS (M + 1) 287. |
| 287 | N-{2-[(2-methylpropyl)amino]pyrid-5-yl}-4-oxo-4,5,6,7-tetrahydro-1H-indole-3-carboxamide | 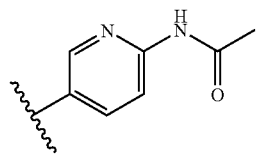 | M.W. 326.402; MS (M + 1) 327 |
| 288 | N-[2-(acetamido)pyrid-5-yl]-4-oxo-4,5,6,7-tetrahydro-1H-indole-3-carboxamide | 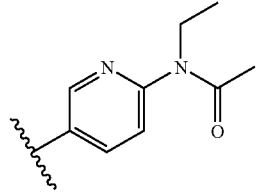 | M.W. 312.332; MS (M + 1) 313. |
| 289 | N-[2-(N-ethylacetamido)pyrid-5-yl]-4-oxo-4,5,6,7-tetrahydro-1H-indole-3-carboxamide | | M.W. 340.386; MS (M + 1) 341 |
| 290 | N-{2-[2-(morpholin-4-yl)ethylamino]pyrid-5-yl}-4-oxo-4,5,6,7-tetrahydro-1H-indole-3-carboxamide | 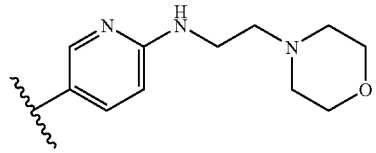 | M.W. 383.450; MS (M + 1) 384 |

TABLE I-continued

| Cmd # | Name | G | Spectral Data |
|---|---|---|---|
| 291 | N-(2-{[2-(N-methylacetamido)ethyl]amino}pyrid-5-yl)-4-oxo-4,5,6,7-tetrahydro-1H-indole-3-carboxamide | | M.W. 369.428; MS (M + 1) 370. |
| 292 | N-(2-ethoxy-4-methylpyrid-5-yl)-4-oxo-4,5,6,7-tetrahydro-1H-indole-3-carboxamide | | M.W. 313.360; MS (M + 1) 314. |
| 304 | 4-Oxo-4,5,6,7-tetrahydro-1H-indole-3-carboxylic acid{4-[2-(thiophene-2-sulfonylamino)-ethoxy]phenyl}-amide | | |
| 305 | 4-Oxo-4,5,6,7-tetrahydro-1H-indole-3-carboxylic acid(4-[1,2,4]-triazol-1-yl-phenyl)-amide | | LRMS calcd 321; found [M + 1] 322 |
| 306 | 4-Oxo-4,5,6,7-tetrahydro-1H-indole-3-carboxylic acid{4-[3-(1-methyl-1H-imidazole-4-sulfonylamino)-propoxy]-phenyl}amide | | LRMS calcd 471; found [M + 1] 472 |
| 307 | 4-Oxo-4,5,6,7-tetrahydro-1H-indole-3-carboxylic acid imidazo[1,2-a]pyridin-5-ylamide | | LRMS calcd 294; found [M + 1] 295 |

TABLE I-continued

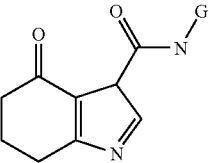

| Cmd # | Name | G | Spectral Data |
|---|---|---|---|
| 308 | 4-Oxo-3a,4,5,6,7,7a-hexahydro-1H-indole-3-carboxylic acid[6-(3-propyl-[1,2,4]thidazol-5-ylamino)-pyridin-2-yl]amide | | $^1$H NMR (CD$_3$OD) 0.75–0.95(m, 3H), 1.62–1.81(m, 5H), 2.60–2.75(m, 5H), 6.07(d, 1H)8.6(s, 1H) LCMS found [M + H] 305.2 |

TABLE II

| Cmd. # | Name | G | Spectral Data |
|---|---|---|---|
| 293 | N-[6-(2-pyridin-3-yl-ethylamino)-pyridin-2-yl]-4-oxo-3a,4,5,6,7,7a-hexahydro-1H-indole-3-carboxylic acidamide | | LCMS found (M + H) 299.3 |
| 294 | N-[6-(3-imidazol-1-yl-propylamino)-pyridin-2-yl)-4-oxo-3a,4,5,6,7,7a-hexahydro-1H-indole-3-carboxamide | | LCMS found (M + H) 379.3 |
| 295 | N-[6-(3-propyl[1,2,4]thiadiazol-5-ylamino)-pyridin-2-yl]-4-oxo-3a,4,5,6,7,7a-hexahydro-1H-indole-3-carboxamide | | LCMS found (M + H) 305.2 |
| 296 | N-(6-ethylaminopyridin-2-yl)-4-oxo-3a,4,5,6,7,7a-hexahydro-1H-indole-3-carboxylic acid | | LCMS found (M + H) 299.3 |
| 297 | 4-oxo-3a,4,5,6,7,7a-hexahydro-1H-indole-3-carboxylic acid{6-(2-ethyl-imidazol-1yl)ethoxy)-pyridin-3-yl}amide | | LCMS found (M + H) 394.4 |

TABLE II-continued

| Cmd. # | Name | G | Spectral Data |
|---|---|---|---|
| 298 | 4-oxo-3a,4,5,6,7,7a-hexahydro-1H-indole-3-carboxylic acid[6-(2-imidazol-1-yl-ethoxy)-pyridin-3-yl]-amide | (5-pyridyl with 6-O-CH2CH2-imidazol-1-yl) | LCMS found (M + H) 366.4 |

Example 5

Intermediate Compounds

The intermediate compounds shown in TABLE III are prepared using the methods given in Schemes III and IV.

Example 5

Water solubility for various compounds within the invention was determined and compared with that for compounds outside the scope of the invention. The compounds evaluated are encompassed by Formula II:

TABLE III

| Cmp # | Scheme | Name | Structure | Data |
|---|---|---|---|---|
| 299 | 3 | N-Ethyl-pyridine-2,6-diamine | 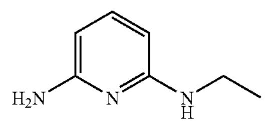 | LCMS found (M + H) 125 |
| 300 | 3 | N-(3-Imidazol-1-yl-propyl)-pyridine-2,6-diamine | 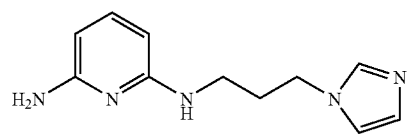 | LCMS found (M + H) 218 |
| 301 | 3 | N-(2-Pyridin-2-yl-ethyl)-pyridine-2,6-diamine | 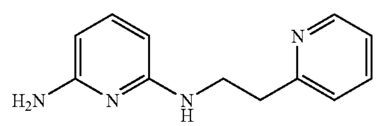 | LCMS found (M + H) 215 |
| 302 | 4 | 4-(2-Imidazol-1-yl-ethoxy)-phenylamine | 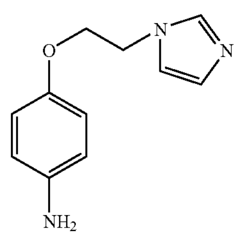 | LCMS found (M + H) 204 |
| 303 | 4 | 4-[2-(2-Ethyl-imidazol-1-yl)-ethoxy]phenylamine | 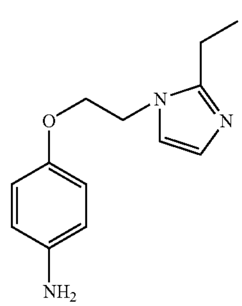 | LCMS found (M + H) 232 |

TABLE IV

Formula II (structure shown: 4-oxo-4,5,6,7-tetrahydroindole-3-carboxamide with Rx, Ry substituents on position 5, (CH2)n in ring, N-R amide)

| Water Solubility (ug/ml) | Rx | Ry | n | R |
|---|---|---|---|---|
| 23 | H | H | 1 | 4-(OCH2CH2OH)-phenyl |
| 203 | H | H | 1 | 3-(CH2NHCH3)-phenyl |
| 143 | H | H | 2 | 4-(CH2NHCH3)-phenyl |
| 15 | H | H | 1 | 4-(CH2NHCH(CH3)2)-phenyl |
| 1.0 | H | H | 1 | 4-F-phenyl |
| 0.58 | H | H | 1 | 4-CH3-phenyl |
| 0.34 | H | H | 1 | 4-OCH2CH3-phenyl |
| 0.26 | CH3 | CH3 | 1 | 3-F-4-OCH3-phenyl |

Example 6

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

Example 7

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 8

Binding Assay

This assay is a standard assay for $GABA_A$ binding affinity. The high affinity and high selectivity of compounds of this invention for the benzodiazepine site of the $GABA_A$ receptor is confirmed using the binding assay described in Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 μl of tissue homogenate, 100 μl of radioligand, (0.5 nM $^{3}H$-Ro15-1788 [$^{3}H$-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 μM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested in this assay preferred compounds of the invention exihibit $K_i$ values of less than 1 uM, more preferred compounds of the invention have $K_i$ values of less than 500 nM, still more preferred compounds of the invention have $K_i$ values of less than 100 nM, and even more preferred compounds have $K_i$ values of less than 10 nM.

Results for several compounds of this invention are listed in Table V.

TABLE V

| Compound Number | $K_i$ (nM) |
|---|---|
| 1 | 90 |
| 2 | 29 |
| 3 | 49 |
| 4 | 0.24 |
| 5 | 9 |
| 6 | 9 |
| 7 | 30 |
| 8 | 27 |
| 9 | 1.3 |
| 10 | 37 |
| 11 | 7 |
| 12 | 5 |
| 13 | 24 |
| 14 | 3 |
| 15 | 12 |

Example 9

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\alpha_2$, GENBANK accession no. M82919; human $\beta_3$, GENBANK accession no. Z20136; human β$_2$, GENBANK accession no. X15376; rat α$_1$, GENBANK accession no. L08490, rat α$_2$, GENBANK accession no. L08491; rat α$_3$, GENBANK accession no. L08492; rat α$_5$, GENBANK accession no. L08494; rat β$_2$, GENBANK accession no. X15467; rat β$_3$, GENBANK accession no. X15468; and rat γ$_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+ test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and EC$_{50}$ values by standard methods. To evaluate average efficacy and EC$_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

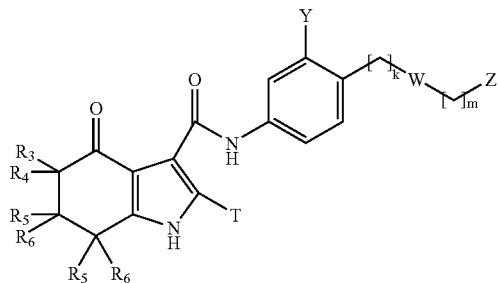

wherein Y is independently selected at each occurrence from hydrogen, hydroxy, halogen, C$_1$-C$_6$ alkyl, C$_1$-C$_6$ alkoxy, cyano, nitro, amino, and mono- or dialkyl (C$_1$-C$_6$) amino;

T is halogen, hydrogen, hydroxyl, amino, alkyl or alkoxy;

W is chosen from —O—, —NH—, —NR$_7$—, —S(O)$_{0-2}$—, —C(=O)—, —OC(=O)—, —C(=O)O—, —C(=O)NH—, —NHC(=O)—, —NR$_7$C(=O)—, —NHS(O)$_{0-2}$—, —NR$_7$S(O)$_{0-2}$—, —S(O)$_{0-2}$NH—, —S(O)$_{0-2}$R$_7$H—, and CR$_7$R$_8$ where R$_7$ and R$_8$ are the same or different and represent hydrogen, alkyl, or R$_7$-R$_8$ taken together represents a cyclic moiety having 3–7 carbon atoms;

Z is hydroxy, cycloalkyl (alkoxy), amino, mono- or di (alkyl$_1$)amino, azacycloalkyl, —O(alkyl$_1$), —S(O)$_{0-2}$(alkyl$_1$), —OC(=O) (alkyl$_1$), —OC(=O)H, —C(=O)O(alkyl$_1$), —C(=O)OH, —C(=O)NH(alkyl$_1$), —C(=O)NH$_2$, —NHC(=O) (alkyl$_1$), —NHC(=O)H, —N(alkyl$_1$)C(=O) (alkyl$_1$), —NHS(O)$_{0-2}$(alkyl$_1$), —N(alkyl$_1$)S(O)$_{0-2}$(alkyl$_1$), —S(O)$_{0-2}$NH(alkyl$_1$), or —S(O)$_{0-2}$(alkyl$_1$)N(alkyl$_1$), wherein alkyl$_1$ is independently chosen at each occurrence and is straight, branched, or cyclic, may contain one or two double or triple bonds, and is unsubstituted or substituted with one or more substitutents selected from: hydroxy, oxo, halogen, amino, cyano, nitro, and alkoxy, or Z is phenyl or phenylalkyl where the phenyl portion is optionally substituted with alkyl, hydroxy, alkoxy, trifluoromethyl, halogen, amino, or mono- or di-alkylamino, or Z is NR$_9$COR$_{10}$ where R$_9$ and R$_{10}$ are the same or different and represent hydrogen or alkyl or cycloalkyl, or Z is connected, optionally through W, to Q to from a 1–6 membered ring; or Z represents a group of the formula:

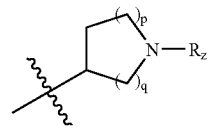

p is 1, 2, or 3;

q is 0, 1, or 2; and

R$_z$ is hydrogen or alkyl; or

Z is a group of the formula:

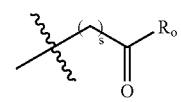

where s is 0, 1, 2 or 3, and the sum of s and m is not less than 1;

R$_o$ is hydroxy, C$_1$-C$_6$ alkoxy, amino, mono- or di-alkylamino where each alkyl is independently optionally substituted with amino, mono- or dialkylamino, or R$_o$ is a group of the formula

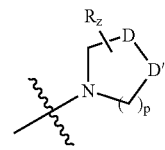

where p, D, D', and $R_z$ are as defined above;

and independently represent a carbon chain optionally substituted with hydrogen, halogen, oxo, cyano, nitro, amino, mono or dialkylamino, straight or branched chain alkyl, alkenyl, alkynyl, trifluoromethyl, trifluoromethoxy, or cycloalkyl; wherein k is 0, 1, 2, or 3;

m is 0, 1, 2, or 3; and $R_3$, $R_4$, $R_5$, and $R_6$ are the same or different and are independently selected at each occurrence from hydrogen, alkyl, $-COR_{11}$ or $-CO_2R_{11}$ where $R_{11}$ is alkyl or cycloalkyl having 3–7 carbon atoms; or $-CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or $R_3$-$R_4$ are taken together to form a cyclic moiety having 3–7 carbon atoms; or $R_5$-$R_6$ are taken together to form a cyclic moiety having 3–7 carbon atoms;

where each alkyl group forming an $R_3$, $R_4$, $R_5$, or $R_6$ substituent or portion thereof may be substituted independently with hydroxy or mono- or dialkylamino where each alkyl is independently alkyl or cycloalkyl.

2. A compound according to claim 1, of the formula:

wherein Y is independently selected at each occurrence from hydrogen, hydroxy, halogen, $C_1$-$C_6$ alkyl, $C_1$-$C_6$ alkoxy, cyano, nitro, amino, and mono- or dialkyl($C_1$-$C_6$)amino.

3. A compound according to claim 1, of the formula:

wherein Y is independently selected at each occurrence from hydroxy, halogen, $C_1$-$C_6$ alkyl, $C_1$-$C_6$ alkoxy, cyano, nitro, amino, and mono- or dialkyl($C_1$-$C_6$)amino.

4. A compound of the formula:

or a pharmaceutically acceptable salt thereof wherein:

T is halogen, hydrogen, hydroxyl, amino, alkyl or alkoxy;

X is hydrogen, hydroxy, amino, benzyl, t-butoxycarbonyl, benzyloxycarbonyl, alkyl, or alkoxy;

G represents or ;

W is oxygen or methylene;

Z is oxygen, nitrogen, or methylene;

m is 1 or 2;

n is 0, 1, 2, or 3; and $R_3$, $R_4$, $R_5$, and $R_6$ are the same or different and are independently selected at each occurrence from hydrogen, alkyl, $-COR_{11}$ or $-CO_2R_{11}$ where $R_{11}$ is alkyl or cycloalkyl having 3–7 carbon atoms; or $-CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or $R_3$ and $R_4$ together with the carbon atom to which they are attached form a cyclic moiety having 3–7 carbon atoms; or $R_5$ and $R_6$ together with the carbon atom to which they are attached form a cyclic moiety having 3–7 carbon atoms;

where each alkyl group forming an $R_3$, $R_4$, $R_5$, or $R_6$ substituent or portion thereof may be substituted independently with hydroxy or mono- or dialkylamino where each alkyl is independently alkyl or cycloalkyl.

5. A compound according to claim 4, of the formula:

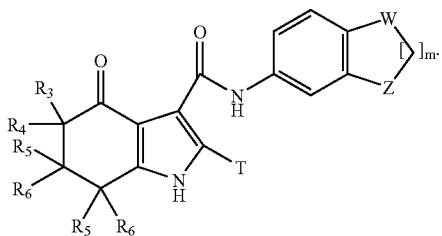

6. A compound according to claim 4, of the formula:

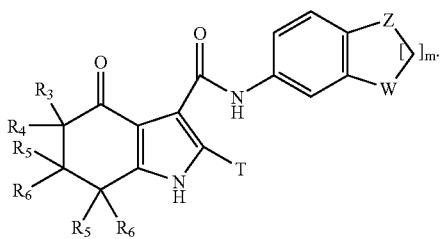

7. A compound according to claim 4, of the formula:

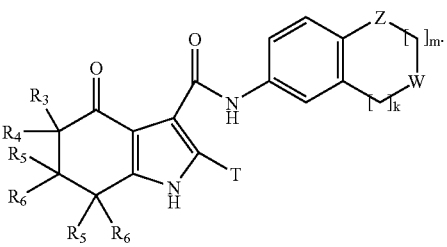

8. A compound according to claim 4, of the formula:

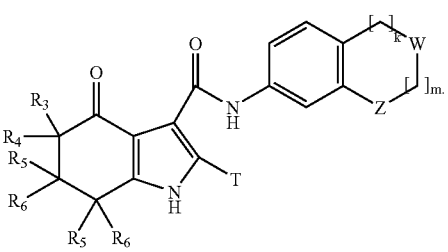

9. A compound of the formula:

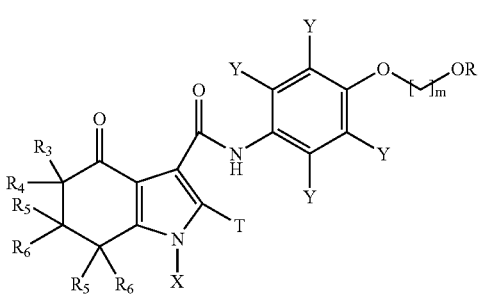

wherein:

R is hydrogen or alkyl wherein the alkyl is straight, branched, or cyclic, may contain one or two double and/or triple bonds, and is unsubstituted or substituted with one or more substituents selected from hydroxy, oxo, halogen, amino, cyano, nitro, and alkoxy;

each Y is independently selected from hydrogen, hydroxy, halogen, $C_1$-$C_6$ alkyl, $C_1$-$C_6$ alkoxy, cyano, nitro, amino, and mono- or dialkyl($C_1$-$C_6$)amino;

T is halogen, hydrogen, hydroxyl, amino, alkyl or alkoxy;

X is hydrogen, hydroxy, amino, benzyl, t-butoxycarbonyl, benzyloxycarbonyl, alkyl, or alkoxy;

m is 1–3; and $R_3$, $R_4$, $R_5$, and $R_6$ are the same or different and are independently selected at each occurrence from hydrogen, alkyl, —$COR_{11}$ or —$CO_2R_{11}$ where $R_{11}$ is alkyl or cycloalkyl having 3–7 carbon atoms; or —$CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or $R_3$ and $R_4$ together with the carbon atom to which they are attached form a cyclic moiety having 3–7 carbon atoms; or $R_5$ and $R_6$ together with the carbon atom to which they are attached form a cyclic moiety having 3–7 carbon atoms;

where each alkyl group forming an $R_3$, $R_4$, $R_5$, or $R_6$ substituent or portion thereof may be substituted independently with hydroxy or mono- or dialkylamino where each alkyl is independently alkyl or cycloalkyl.

10. A compound according to claim 9, of the formula:

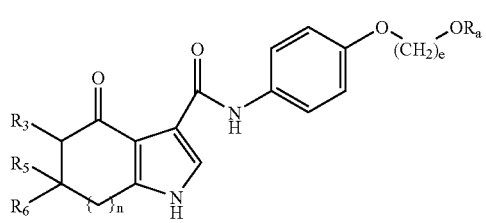

where $R_3$, $R_5$, and $R_6$ independently represent hydrogen or alkyl;

$R_a$ represents hydrogen or alkyl where the alkyl is optionally halogenated; and e is an integer of 1–3.

11. A compound according to claim 9, of the formula:

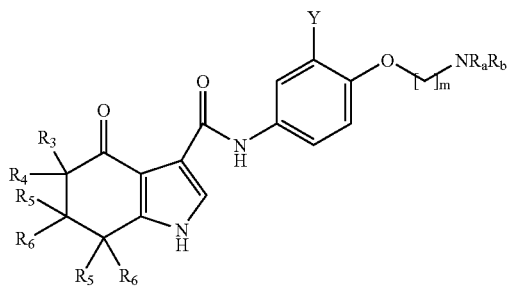

wherein:

$R_a$ and $R_b$ are independently hydrogen or alkyl wherein each alkyl is independently straight, branched, or cyclic, may contain one or two double or triple bonds, and is unsubstituted or substituted with one or more substitutents selected from: hydroxy, oxo, halogen, amino, cyano, nitro, and alkoxy; or $R_a$ and $R_b$ are joined to form a heterocycloalkyl ring; and Y is independently selected at each occurrence from hydrogen, hydroxy, halogen, $C_1$-$C_6$ alkyl, $C_1$-$C_6$ alkoxy, cyano, nitro, amino, and mono- or dialkyl($C_1$-$C_6$)amino.

12. A compound of the formula:

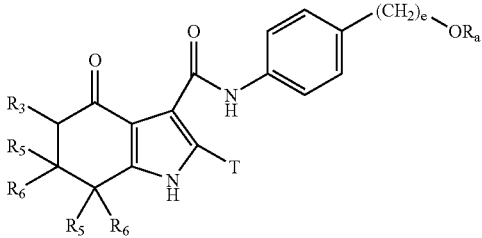

where $R_3$, $R_5$, and $R_6$ independently represent hydrogen, or alkyl;

$R_a$ represents hydrogen or alkyl where the alkyl is optionally halogenated;

T is halogen, hydrogen, hydroxyl, amino, alkyl or alkoxy; and e is an integer of 1–3.

13. A compound according to claim 4, of the formula:

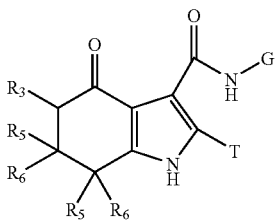

where G represents:

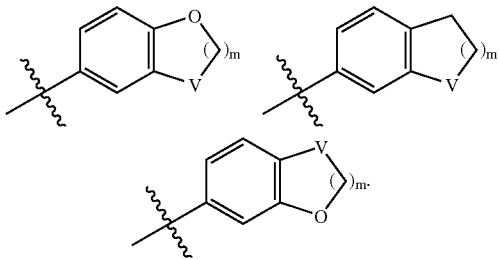

where V is oxygen, nitrogen, or methylene; and m is 1 or 2.

14. A compound which is
N-[4-(2-Pyrrolidinylethoxy)phenyl]-4-oxo-4,5,6,7-tetrahydro-1H-indole-3-carboxamide; or
N-{3-[2-(3-Trifluoromethylbenzylamino)ethoxy]phenyl}-4-oxo-4,5,6,7-tetrahydro-1H-indole-3-carboxamide.

15. A compound which is
N-{3-[3-(3-Trifluoromethylbenzylamino)propoxy]phenyl}-4-oxo-4,5,6,7-tetrahydro-1H-indole-3-carboxamide;
N-[4-(2-Pyrrolidin-1-ylethyl)phenyl]-4-oxo-4,5,6,7-tetrahydro-1H-indole-3-carboxamide;

N-[2-Fluoro-4-(2-n-propylaminoethoxy)phenyl]-4-oxo-4,5,6,7-tetrahydro-1H-indole-3-carboxamide; or
N-[3-Fluoro-4-(2-n-propylaminoethoxy)phenyl]-4-oxo-4,5,6,7-tetrahydro-1H-indole-3-carboxamide.

16. A compound according to claim 1 which is
N-[3-Fluoro-4-(2-n-propylaminoethoxy)phenyl]-4-oxo-4,5,6,7-tetrahydro-1H-indole-3-carboxamide hydrochloride;
N-[3-Fluoro-4-(2-Cyclopropylmethylaminoethoxy)phenyl]-4-oxo-4,5,6,7-tetrahydro-1H-indole-3-carboxamide; or
N-[3-Fluoro-4-(2-Cyclopropylmethylaminoethoxy)phenyl]-4-oxo-4,5,6,7-tetrahydro-1H-indole-3-carboxamide tosylate.

17. A compound which is
N-[3-Fluoro-4-(2-Isobutylaminoethoxy)phenyl]-4-oxo-4,5,6,7-tetrahydro-1H-indole-3-carboxamide;
N-[3-Fluoro-4-(2-n-butylaminoethoxy)phenyl]-4-oxo-4,5,6,7-tetrahydro-1H-indole-3-carboxamide;
N-[3-Fluoro-4-(2-t-butylaminoethoxy)phenyl]-4-oxo-4,5,6,7-tetrahydro-1H-indole-3-carboxamide;
N-[4-(2-adamant-2-ylaminoethoxy)phenyl]-4-oxo-4,5,6,7-tetrahydro-1H-indole-3-carboxamide;
N-{4-[(R)-Pyrrolidin-2-ylmethoxy]phenyl}-4-oxo-4,5,6,7-tetrahydro-1H-indole-3-carboxamide;
N-{4-[(S)-Pyrrolidin-2-ylmethoxy]phenyl}-4-oxo-4,5,6,7-tetrahydro-1H-indole-3-carboxamide; or
N-[4-(Piperidin-3-ylmethoxy)phenyl]-4-oxo-4,5,6,7-tetrahydro-1H-indole-3-carboxamide.

18. A compound which is
N-[4-(Piperidin-3-ylmethoxy)phenyl]-4-oxo-4,5,6,7-tetrahydro-1H-indole-3-carboxamide hydrochloride;
N-[3-Fluoro-4-(2-dimethylaminoethoxy)phenyl]-4-oxo-4,5,6,7-tetrahydro-1H-indole-3-carboxamide;
N-[4-(2-Pyrrolidin-1-ylethoxy)phenyl]-4-oxo-4,5,6,7-tetrahydro-1H-indole-3-carboxamide;
N-[3-Fluoro-4-(2-pyrrolidin-1-ylethoxy)phenyl]-4-oxo-4,5,6,7-tetrahydro-1H-indole-3-carboxamide;
N-[4-(2-Piperidin-2-ylethoxy)phenyl]-4-oxo-4,5,6,7-tetrahydro-1H-indole-3-carboxamide;
N-{4-[3-(2,2,2,-Trifluorethyl)aminopropoxy]phenyl}-4-oxo-4,5,6,7-tetrahydro-1H-indole-3-carboxamide; or
N-{4-[2-(4-Methylaminopiperizin-1 yl)-2-oxo-ethyl]phenyl}-4-oxo-4,5,6,7-tetrahydro-1H-indole-3-carboxamide.

19. A compound according to claim 1, which is
N-[3-Fluoro-4-(2-hydroxy-2-oxoethoxy)phenyl]-4-oxo-4,5,6,7-tetrahydro-1H-indole-3-carboxamide;
N-[3-Fluoro-4-(2-ethylamino-2-oxoethoxy)phenyl]-4-oxo-4,5,6,7-tetrahydro-1H-indole-3-carboxamide;
N-[3-Fluoro-4-(2-diethylamino-2-oxoethoxy)phenyl]-4-oxo-4,5,6,7-tetrahydro-1H-indole-3-carboxamide; or
N-{3-Fluoro-4-[2-(4-methylpiperizin-1-yl)-2-oxoethoxy]phenyl}-4-oxo-4,5,6,7-tetrahydro-1H-indole-3-carboxamide.

20. A compound which is
N-ethyl-N-[2-(ethylamino)ethyl]-2-{4-[(4-oxo-(4,5,6,7-tetrahydroindol-3-yl))carbonylamino]phenoxy}acetamide;
N-[2-(dipropylamino)ethyl]-2-{4-[(4-oxo-(4,5,6,7-tetrahydroindol-3-yl))carbonylamino]phenoxy}acetamide;
N-[2-(diethylamino)ethyl]-N-methyl-2-{4-[(4-oxo-(4,5,6,7-tetrahydroindol-3-yl))carbonylamino]phenoxy}acetamide;

N-[2-(diethylamino)ethyl]-N-ethyl-2-{4-[(4-oxo-(4,5,6,7-tetrahydroindol-3-yl))carbonylamino]phenoxy}acetamide;

N-[3-fluoro-4-(2-morpholin-4-yl-2-oxoethoxy)phenyl](4-oxo-(4,5,6,7-tetrahydroindol-3-yl))carboxamide;

(4-oxo-(4,5,6,7-trihydroindol-3-yl))-N-[4-(2-oxo-2-piperazinylethoxy)phenyl]carboxamide;

N-[3-(diethylamino)propyl]-2-{4-[(4-oxo-(4,5,6,7-tetrahydroindol-3-yl))carbonylamino]phenoxy}acetamide;

N-[3-(diethylamino)propyl]-2-{2-fluoro-4-[(4-oxo-(4,5,6,7-tetrahydroindol-3-yl))carbonylamino]phenoxy}acetamide; or N-[4-(diethylamino)-1-methylbutyl]-2-{4-[(4-oxo-(4,5,6,7-tetrahydroindol-3-yl))carbonylamino]phenoxy}acetamide.

21. A compound of the formula:

or the pharmaceutically acceptable non-toxic salts thereof wherein:

Q is phenyl which may be mono or disubstituted with hydroxy or halogen;

T is halogen, hydrogen, hydroxyl, amino, alkyl or alkoxy;

W is oxygen or nitrogen;

Z is $C_3$-$C_7$ azacycloalkyl, —O($C_1$-$C_6$ alkyl$_1$), —S(O)$_{0-2}$ ($C_1$-$C_6$ alkyl$_1$), —C(=O) ($C_1$-$C_6$ alkyl$_1$), —OC(=O) ($C_1$-$C_6$ alkyl$_1$), —OC(=O)H, —C(=O)O($C_1$-$C_6$ alkyl$_1$), —C(=O)OH, —C(=O)NH($C_1$-$C_6$ alkyl$_1$), —C(=O)NH$_2$, —NHC(=O) ($C_1$-$C_6$ alkyl$_1$), —NHC(=O)H, —N($C_1$-$C_6$ alkyl$_1$)C(=O) ($C_1$-$C_6$ alkyl$_1$), —NHS(O)$_{0-2}$($C_1$-$C_6$ alkyl$_1$), —N($C_1$-$C_6$ alkyl$_1$)S(O)$_{0-2}$ ($C_1$-$C_6$ alkyl$_1$), —S(O)$_{0-2}$NH($C_1$-$C_6$ alkyl$_1$), or —S(O)$_{0-2}$($C_1$-$C_6$ alkyl$_1$)N($C_1$-$C_6$ alkyl$_1$), wherein $C_1$-$C_6$ alkyl$_1$ is independently chosen at each occurrence and is straight, branched, or cyclic, may contain one or two double or triple bonds, and is unsubstituted or substituted with one or more substitutents selected from: hydroxy, oxo, halogen, amino, cyano, nitro, and alkoxy, or Z is phenyl or phenyl($C_1$-$C_6$)alkyl where the phenyl portion is optionally substituted with $C_1$-$C_6$ alkyl, hydroxy, $C_1$-$C_6$ alkoxy, trifluoromethyl, trifluoromethoxy, halogen, amino, or mono- or di$C_1$-$C_6$ alkylamino, or Z represents a group of the formula:

where p is 1, 2, or 3;

D and D' independently represent oxygen, NR$_y$ or CHR$_y$, provided that only one of D and D' may be NR$_y$, where each R$_y$ is hydrogen or $C_1$-$C_6$ alkyl; or and R$_z$ is hydrogen or $C_1$-$C_6$ alkyl, or Z represents a group of the formula:

where p is 1, 2, or 3;

q is 0, 1, or 2;

R$_z$ is hydrogen or $C_1$-$C_6$ alkyl; or

Z is a group of the formula:

where s is 0, 1, 2 or 3, and the sum of s and m is not less than 1;

R$_o$ is hydroxy, $C_1$-$C_6$ alkoxy, amino, mono- or di$C_1$-$C_6$ alkylamino where each alkyl is independently optionally substituted with amino, mono- or di$C_1$-$C_6$ alkylamino, or R$_o$ is a group of the formula where p, D, D', and R$_z$ are as defined above;

and independently represent a carbon chain optionally substituted with hydrogen, halogen, oxo, cyano, nitro, amino, mono or di($C_1$-$C_6$)alkylamino, straight or branched chain $C_1$-$C_6$ alkyl, $C_2$-$C_6$ alkenyl, $C_2$-$C_6$ alkynyl, trifluoromethyl, trifluoromethoxy, or cyclo$C_1$-$C_6$ alkyl;

wherein k is 0, 1, 2, or 3;

m is 0, 1, 2, or 3; and represents a carbon chain optionally substituted with R$_5$ and R$_6$ and n is 0, 1, 2, or 3;

R$_3$, R$_4$, R$_5$, and R$_6$ are the same or different and are independently selected at each occurrence from hydrogen, $C_1$-$C_6$ alkyl, —COR$_{11}$ or —CO$_2$R$_{11}$ where R$_{11}$ is $C_1$-$C_6$ alkyl or $C_3$-$C_7$ cycloalkyl; or —CONR$_{12}$R$_{13}$ where R$_{12}$ and R$_{13}$ are selected independently from hydrogen, C$_1$-C$_6$ alkyl, C$_3$-C$_7$ cycloalkyl, phenyl, 2-, 3-, or 4-pyridyl, or NR$_{12}$R$_{13}$ forms a heterocyclic group which is morpholinyl, piperidinyl, pyrrolidinyl, or N-alkyl piperazinyl; or R$_3$-R$_4$ are taken together to form a cyclic moiety having 3–7 carbon atoms; or R$_5$-R$_6$ are taken together to form a cyclic moiety having 3–7 carbon atoms; and where each alkyl group forming an R$_3$, R$_4$, R$_5$, or R$_6$ substitutent or portion thereof may be substituted independently with hydroxy or mono- or dialkylamino where each alkyl is independently C$_3$-C$_7$ alkyl or cycloalkyl having 3–7 carbon atoms.

22. A compound of formula A:

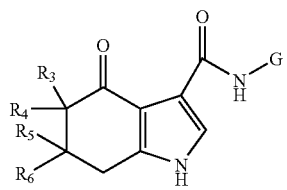

or a pharmaceutically acceptable salt thereof wherein

R$_3$, R$_4$, R$_5$, and R$_6$ are the same or different and are selected from hydrogen, alkyl, —COR$_{11}$ or —CO$_2$R$_{11}$ where R$_{11}$ is alkyl or cycloalkyl having 3–7 carbon atoms; or —CONR$_{12}$R$_{13}$ where R$_{12}$ and R$_{13}$ are selected independently from hydrogen, alkyl, cycloalkyl having 3–7 carbon atoms, phenyl, 2-, 3-, or 4-pyridyl, or NR$_{12}$R$_{13}$ forms a heterocyclic group which is morpholinyl, piperidinyl, pyrrolidinyl, or N-alkyl piperazinyl; or R$_3$-R$_4$ are taken together to form a cyclic moiety having 3–7 carbon atoms; or R$_5$-R$_6$ are taken together to form a cyclic moiety having 3–7 carbon atoms; and where each alkyl group forming an R$_3$, R$_4$, R$_5$, or R$_6$ substituent or portion thereof may be substituted independently with hydroxy or mono- or dialkylamino where each alkyl is independently alkyl or cycloalkyl having 3–7 carbon atoms; and G represents

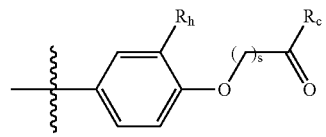

where

R$_h$ is hydorgen, halogen, C$_1$-C$_6$ alkyl, C$_1$-C$_6$ alkoxy, or trifluoromethyl;

s is 0, 1, 2 or 3, and the sum of s and m is not less than 1;

R$_o$ is hydroxy, C$_1$-C$_6$ alkoxy, amino, mono- or diC$_1$-C$_6$ alkylamino where each alkyl is independently optionally substituted with amino, mono- or diC$_1$-C$_6$ alkylamino, or R$_o$ is a group of the formula

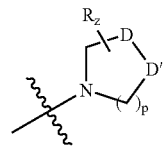

p is 1, 2, or 3;

D and D' independently represent oxygen, NR$_y$ or CHR$_y$, provided that only one of D and D' may be NR$_y$, where each R$_y$ is hydrogen or C$_1$-C$_6$ alkyl; or and R$_z$ is hydrogen or C$_1$-C$_6$ alkyl.

23. A compound according to claim 22, wherein R$_h$ is hydrogen or halogen, and R$_o$ is a group of the formula:

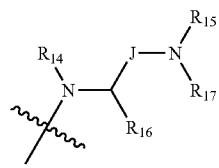

where

R$_{14}$ is hydrogen or C$_1$-C$_6$ alkyl;

R$_{15}$ is hydrogen or C$_1$-C$_6$ alkyl;

R$_{16}$ is hydrogen, ethyl, or methyl;

R$_{17}$ is C$_1$-C$_6$ alkyl; and

J is a C$_1$-C$_4$ alkylene group.

24. A compound according to claim 22, wherein s is 1 and R$_o$ is ethoxy, hydroxy, ethylamino, diethylamino, morpholinyl, piperazinyl, 4-methylpiperazinyl,

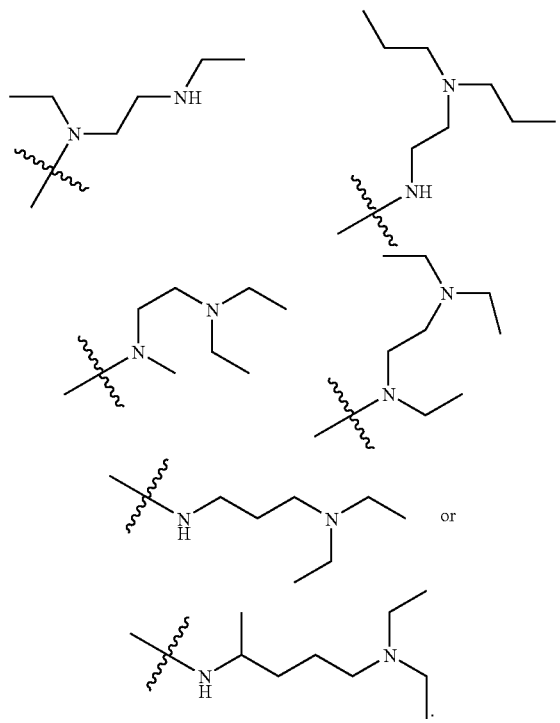

25. A pharmaceutical composition comprising a compound according to claim 4 combined with at least one pharmaceutically acceptable carrier or excipient.

26. A method for the treatment of a disease or disorder associated with pathogenic agonism, inverse agonism or antagonism of the $GABA_A$ receptor, said method comprising administering to a patient in need of such treatment an effective amount of a compound of claim 4.

27. A method according to claim 26 wherein the disease or disorder associated with pathogenic agonism, inverse agonism or antagonism of the $GABA_A$ receptor is anxiety, depression, a sleep disorder, or cognitive impairment.

28. A method for localizing $GABA_A$ receptors in a tissue sample comprising contacting with the sample a detectably-labeled compound of claim 4 under conditions that permit binding of the compound to $GABA_A$ receptors, washing the sample to remove unbound compound, and detecting the bound compound.

29. A method of inhibiting the binding of a benzodiazepine compound to a $GABA_A$ receptor, said method comprising contacting a compound of claim 4 with cells expressing such a receptor in the presence of the benzodiazepine, wherein the compound is present at a concentration sufficient to inhibit the binding a benzodiazepine compound to a $GABA_A$ receptor in vitro.

30. A packaged pharmaceutical composition comprising the pharmaceutical composition of claim 4 in a container and instructions for using the composition to treat a patient suffering from a disorder responsive to agonism, inverse agonism or antagonism of the $GABA_A$ receptor.

31. The packaged pharmaceutical composition of claim 30, wherein said patient is suffering from anxiety, depression, a sleep disorder, cognitive impairment, or Alzheimer's dementia.

32. A compound of the formula:

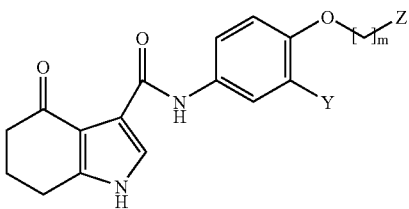

wherein
Y is halogen;
m is 1, 2 or 3; and
Z is amino or mono or dialkylamino.

33. A compound according to claim 32 wherein Z is monoalkylamino, m is 2, and Y is fluorine.

34. A compound of the formula:

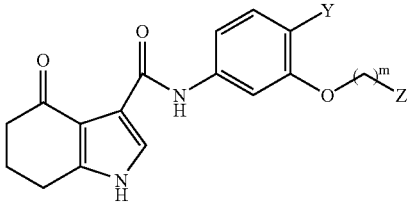

wherein
Y is hydrogen, halogen or hydroxy;
m is 1, 2 or 3; and
Z is amino or mono or dialkylamino.

35. A compound according to claim 10 wherein n is 1.

36. A method for altering the signal-transducing activity of $GABA_A$ receptors, said method comprising exposing cells expressing such receptors to a compound according to claim 4 at a concentration sufficient to inhibit RO15-1788 binding to cells expressing a cloned human $GABA_A$ receptor in vitro.

* * * * *